(12) United States Patent
Sanders et al.

(10) Patent No.: US 9,017,963 B2
(45) Date of Patent: *Apr. 28, 2015

(54) METHOD FOR DETECTING MICROORGANISMS

(75) Inventors: Mitchell C. Sanders, West Boylston, MA (US); Adrian M. Lowe, Newton, MA (US); Maureen A. Hamilton, Littleton, MA (US); Gerard J. Colpas, Holden, MA (US)

(73) Assignee: Woundchek Laboratories (US), Inc., Fall River, MA (US)

( * ) Notice: Subject to any disclaimer, the term of this patent is extended or adjusted under 35 U.S.C. 154(b) by 1508 days.

This patent is subject to a terminal disclaimer.

(21) Appl. No.: 10/502,882

(22) PCT Filed: Jan. 31, 2003

(86) PCT No.: PCT/US03/03172
§ 371 (c)(1),
(2), (4) Date: Feb. 23, 2005

(87) PCT Pub. No.: WO03/063693
PCT Pub. Date: Aug. 7, 2003

(65) Prior Publication Data
US 2005/0142622 A1    Jun. 30, 2005

Related U.S. Application Data

(60) Provisional application No. 60/354,001, filed on Jan. 31, 2002, provisional application No. 60/383,847, filed on May 28, 2002.

(51) Int. Cl.
*C12Q 1/14* (2006.01)
*C12Q 1/04* (2006.01)
(Continued)

(52) U.S. Cl.
CPC .. *C12Q 1/04* (2013.01); *C12Q 1/37* (2013.01); *C12Q 1/54* (2013.01); *C12Q 1/10* (2013.01); *C12Q 1/14* (2013.01); *C12Q 1/34* (2013.01); *C12Q 1/44* (2013.01)

(58) Field of Classification Search
CPC ............... C12Q 1/04; C12Q 1/10; C12Q 1/14
USPC .......................................................... 435/36
See application file for complete search history.

(56) References Cited

U.S. PATENT DOCUMENTS

| 4,242,447 A | 12/1980 | Findl et al. |
| 4,259,442 A | 3/1981 | Gayral |

(Continued)

FOREIGN PATENT DOCUMENTS

| DE | 1 961 7338 | 11/1997 |
| EP | 0 122 028 A1 | 10/1984 |

(Continued)

OTHER PUBLICATIONS

Holliday, M.G., et al., 1999, Journal of Clinical Microbiology, 38, 1190-1192.*

(Continued)

*Primary Examiner* — Sharmila G. Landau
*Assistant Examiner* — Sheridan Macauley
(74) *Attorney, Agent, or Firm* — McDonnell Boehnen Hulbert & Berghoff LLP

(57) ABSTRACT

Described herein are methods of detecting a wound infection and for detecting the presence or absence of microorganisms, for example, wound pathogens in a sample, by contacting a sample with an enzyme produced and/or secreted by the bacteria, and detecting modification or the absence of modification of the substrate, as an indicator of the presence or absence of the enzyme in the sample. The present invention also features a biosensor for detecting the presence or absence of bacteria in a sample.

10 Claims, 23 Drawing Sheets

(51) Int. Cl.

| | | |
|---|---|---|
| C12Q 1/02 | (2006.01) | |
| C12Q 1/00 | (2006.01) | |
| C12Q 1/37 | (2006.01) | |
| C12Q 1/54 | (2006.01) | |
| C12Q 1/10 | (2006.01) | |
| C12Q 1/34 | (2006.01) | |
| C12Q 1/44 | (2006.01) | |

(56) References Cited

U.S. PATENT DOCUMENTS

| | | |
|---|---|---|
| 4,693,972 A | 9/1987 | Mansour et al. |
| 4,897,444 A | 1/1990 | Brynes et al. |
| 5,098,830 A | 3/1992 | Bar-Or et al. |
| 5,124,254 A | 6/1992 | Hewlins et al. |
| 5,137,811 A | 8/1992 | Tanaka et al. |
| 5,210,022 A | 5/1993 | Roth et al. |
| 5,236,827 A | 8/1993 | Sussman et al. |
| 5,330,889 A | 7/1994 | Monget |
| 5,393,514 A | 2/1995 | Pitner et al. |
| 5,512,429 A | 4/1996 | Wilton |
| 5,512,445 A | 4/1996 | Yang et al. |
| 5,516,638 A | 5/1996 | Urnovitz et al. |
| 5,518,894 A | 5/1996 | Berg |
| 5,523,205 A | 6/1996 | Cossart et al. |
| 5,662,905 A | 9/1997 | Siadak et al. |
| 5,695,928 A | 12/1997 | Stewart |
| 5,716,799 A | 2/1998 | Rambach |
| 5,719,031 A | 2/1998 | Haugland et al. |
| 5,783,410 A | 7/1998 | He et al. |
| 5,798,276 A | 8/1998 | Haugland et al. |
| 5,804,395 A | 9/1998 | Schade et al. |
| 5,824,468 A | 10/1998 | Scherer et al. |
| 5,846,737 A | 12/1998 | Kang |
| 5,888,725 A | 3/1999 | Sanders |
| 5,888,760 A | 3/1999 | Godsey |
| 5,932,415 A | 8/1999 | Schubert et al. |
| 5,976,827 A | 11/1999 | Jeffrey et al. |
| 5,994,059 A | 11/1999 | Hogan et al. |
| 6,017,711 A | 1/2000 | Gilson et al. |
| 6,048,688 A | 4/2000 | Korth et al. |
| 6,051,391 A | 4/2000 | Schabert et al. |
| 6,087,325 A | 7/2000 | Meers et al. |
| 6,113,856 A | 9/2000 | Lawrence et al. |
| 6,207,430 B1 | 3/2001 | Yaver et al. |
| 6,235,285 B1 | 5/2001 | Burnham |
| 6,255,066 B1 | 7/2001 | Louderback |
| 6,284,517 B1 | 9/2001 | Restaino |
| 6,294,177 B1 | 9/2001 | Fattom |
| 6,342,581 B1 | 1/2002 | Rosen et al. |
| 6,380,370 B1 | 4/2002 | Doucette-Stamm et al. |
| 6,387,650 B1 | 5/2002 | Townsend et al. |
| 6,770,451 B2 | 8/2004 | Rouhani et al. |
| 7,244,583 B2 | 7/2007 | Sanders |
| 2002/0015944 A1 | 2/2002 | Poizman et al. |
| 2003/0044996 A1 | 3/2003 | Travers |
| 2003/0096315 A1 | 5/2003 | Sanders |
| 2003/0104390 A1 | 6/2003 | Etienne et al. |
| 2004/0219617 A1 | 11/2004 | Cauci |
| 2004/0265942 A1 | 12/2004 | Slater et al. |
| 2005/0142622 A1 | 6/2005 | Sanders et al. |
| 2005/0181465 A1 | 8/2005 | Sanders |
| 2006/0292646 A1 | 12/2006 | Colpas |
| 2007/0128589 A1 | 6/2007 | Sanders et al. |
| 2007/0269851 A1 | 11/2007 | Sanders et al. |
| 2007/0275423 A1 | 11/2007 | Sebastian et al. |
| 2010/0221758 A1 | 9/2010 | Sanders |

FOREIGN PATENT DOCUMENTS

| | | |
|---|---|---|
| EP | 0 286 434 | 10/1988 |
| EP | 0 428 000 A1 | 5/1991 |
| EP | 0 430 608 A1 | 6/1991 |
| EP | 0 864 864 A1 | 9/1998 |
| EP | 1 103 621 A1 | 5/2001 |
| JP | 55-74798 | 5/1980 |
| JP | 55074798 | 6/1980 |
| JP | 02-046280 | 2/1990 |
| JP | 03-182246 | 8/1991 |
| JP | 11-178567 A | 7/1999 |
| JP | 11178567 | 7/1999 |
| JP | 2000093195 | 4/2000 |
| JP | 2001169799 | 6/2001 |
| JP | 2001299381 | 10/2001 |
| WO | WO 91/16336 A1 | 10/1991 |
| WO | WO 92/16648 A1 | 10/1992 |
| WO | WO 94/24306 A | 10/1994 |
| WO | WO 97/28261 A1 | 8/1997 |
| WO | WO 98/42864 | 10/1998 |
| WO | WO 00/08203 | 2/2000 |
| WO | WO 00/50872 A2 | 8/2000 |
| WO | WO 00/65348 A2 | 11/2000 |
| WO | WO 01/59149 A2 | 8/2001 |
| WO | WO 01/66790 | 9/2001 |
| WO | WO 02/10433 A2 | 2/2002 |
| WO | WO 03/063693 A2 | 8/2003 |
| WO | WO 2004/087942 | 10/2004 |
| WO | WO 2004/094656 | 11/2004 |
| WO | WO 2005/012556 | 2/2005 |
| WO | WO 2005/017191 A2 | 2/2005 |
| WO | WO 2005/021780 A1 | 3/2005 |
| WO | WO 2005/042770 | 5/2005 |
| WO | WO 2005/042771 | 5/2005 |
| WO | WO 2007/009047 A2 | 1/2007 |
| WO | WO 2007/092909 | 8/2007 |

OTHER PUBLICATIONS

Fontana, C., et al., "Twelve Aberrant Strains of *Staphylococcus aureus* subsp. *aureus* from Clinical Specimens," *J. Clin. Micrbiol.*, 31(8): 2105-2109 (1993).

Gaillot, O., et al., "Evaluation of CHROMagar *Staph. aueus*, a New Chromogenic Medium, for Isolation and Presumptive Identification of *Staphylococcus aureus* from Human Clinical Specimens," *J. Clin. Microbiol.*, 38(4): 1587-1591 (2000).

Perry, J.D., et al., "ABC Medium, a New Chromogenic Agar for Selective Isolation of *Salmonella* spp.," *J. Clin. Microbiol.*, 37(3): 766-768 (1999).

"Oxidase test" *Wikipedia*. Last modified May 24, 2007. Print out date Jul. 20, 2007. <http://en.wikipedia.org/wiki/Oxidase_test>.

"Nitrate reductase test." *Wikipedia*. Last modified Apr. 19, 2007. Print out date Jul. 20, 2007. <http://en.wikipedia.org/wiki/Nitrate_reductase_test>.

"Indole test" *Wikipedia*. Last modified Apr. 6, 2007. Print out date Jul. 20, 2007 <http://en.wikipedia.org/wiki/Indole_test>.

"GUS reporter system" *Wikipedia*. Last modified May 14, 2007. Print out date Jul. 20, 2007 <http://en.wikipedia.org/wiki/GUS_reporter_system>.

"7-2 Classic strain testing" *Microbiology and Bacteriology: The world of microbes*. Print out date Jul. 20, 2007 <http://www.bact.wisc.edu/microtextbook/index.php?module=Book&func=displayarticle&art_id=119>.

Yolken, R. H., "Enzymic Analysis for Rapid Detection of Microbial Infection in Human Body Fluids: An Overview," *Clin. Chem.*, 27:(9): 1490-1498 (1981).

Altekruse S.F., et al., "Cheese-Associated Outbreaks of Human Illness in the United States, 1973 to 1992: Sanitary Manufacturing Practices Protect Consumers," *J. Food Prot.*, 61(10):1405-1407(1998).

Dalton C.B., et al., "An Outbreak of Gastroenteritis and Fever Due to *Listeria monocytogenes* in Milk," *N. Engl. J. Med.*, 336(2): 100-105 (1997).

Domann E., et al., "Molecular Cloning, Sequencing, and Identification of a Metalloprotease Gene from *Listeria monocytogenes* That Is Species Specific and Physically Linked to Listeriolysin Gene," *Infection and Immunity*., 59(1):65-72 (1991).

Engel, L.S., et al., "*Pseudomonas aeruginosa* Protease IV Produces Corneal Damage and Contributes to Bacterial Virulence," *Invest. Ophthalmol. Vis. Sci.*,39(3):662-665( 1998).

(56) References Cited

OTHER PUBLICATIONS

Ericsson, H., et al., "An Outbreak of Listeriosis Suspected to Have Been Caused by Rainbow Trout," *J. Clin. Microbiol.*, 35(11):2904-2907(1997).
From the Centers for Disease Control and Prevention. Update: Multistate Outbreak of Listeriosis—United States, 1998-1999. *JAMA*,281(4):317-318(1999).
Gottesman S., "Proteases and Their Targets in *Escherichia coli*," *Annu. Rev. Genet.* 30: 465-506(1996).
Häse C.C. and Finkelstein, R., "Bacterial Extracellular Zinc-Containing Metalloproteases," *Microbiological Reviews.*,57(4):823-837(1993).
Liu Y., et al., "Use of a Fluorescence Plate Reader for Measuring Kinetic Parameters with Inner Filter Effect Correction," *Anal. Biochem.*, 267(2):331-335(1999).
Maeda H. "Role of Microbial Proteases in Pathogenesis,"*Microbiol. Immunol.*, 40(10):685-699(1996).
Marquis H., et al. "Proteolytic Pathways of Activation and Degradation of a Bacterial Phospholipase C during Intracellular Infection by *Listeria monocytogenes*," *J. Cell Biol.*,137(6):1381-1392(1997).
Nair S. et al. "ClpE, a Novel Member of the HSP100 Family, is Involved in Cell Division and Virulence *Listeria monocytogenes*," *Mol. Microbiol.*, 31(1):185-196 (1999).
Pallen M.J. and Wren, B., "The HtrA family of serine proteases," *Mol. Microbiol.* 26(2): 209-221(1997).
Poyart C., et al., "The Zinc Metalloprotease of *Listeria monocytogenes* Is Required for Maturation of Phosphatidylcholine Phospholipase C: Direct Evidence Obtained by Gene Complementation." *Infect. & Immun.*, 61(4) 1576-1580 (1993).
Rodriguez M., et al., "*Evaluation of Proteolytic Activity of Microorganisms Isolated From Dry Cured Ham*," *J. Appl. Microbiol.*, 85(5): 905-912(1998).
Schwartz M.A., and Luna, E., "Binding and Assembly of Actin Filaments by Plasma Membranes from *Dictyostelium discoideum*." J. Cell Biol., 102(6):2067-2075(1986).
Smith G.A., et al., "The Tandem Repeat Domain in the *Listeria monocytogenes* ActA Protein Controls the Rate of Actin-based Motility, the Percentage of Moving Bacteria, and the Localization of Vasodilator-Stimulated Phosphoprotein and Profilin."*J. Cell Biol.*, 135(3): 647-660 (1996).
Trivett T.L.and Meyer, E., "Citrate Cycle and Related Metabolisth of *Listeria monocytogenes*," *J. Bacteriol.* 107(3):770-779 (1971).
Vollmer P., et al. "Novel Pathogenic Mechanism of Microbial Metalloproteinases: Liberation of Membrane-Anchored Molecules in Biologically Active Form Exemplified by Studies with the Human Interleukin-receptor." *Infection and Immunity.*,64(9):3646-3651(1996).
Wang, Y-L, et al., "Analysis of Cytoskeletal Structures by Microinjection of Fluorescent Probes," Eds. S. Grinstein and K. Foskett, in *Noninvasive Techniques in Cell Biology*, pp. 177-212 (1990).
Thompson, J.S., et al., "Rapid Biochemical Test to Identify Verocytotoxin-Positive Strains of *Escherichia coli* Serotype O157," J. Clin. Microbiol. 28(10): 2165-2168 (1990).
Keelan, S.L. and Flower, R., v"Multitest System for Biochemical Identification of *Salmonella, Escherichia coli*, and Other Enterobacteriaceae Isolated from Foods: Collaborative Study," *J. Assoc. Off. Anal. Chem.* 71(5): 968-972 (1988).
Braun, V. and Schmitz, G., "Excretion of a Protease by *Serratia marcescens*," *Arch. Microbiol.*, 124:55-61, (1980).
Decedue, C.J., et al., "Purification and Characterization of the Extracellular Proteinase of *Serratia marcescens*," *Biochim. Biophys. Acta*, 569:293-301, (1979).
Kennedy, E.P. and Scarborough, G.A., "Mechanism of Hydrolysis of O-Nitrophenyl-β-Galactoside in *Staphylococcus aureus* and Its Significance for Theories of Sugar Transport," *Proc. Natl. Acad. Sci. USA*, 58:225-228 (1967).
Molla, A., et al., "Characterization of 73kDa Thiol Protease from *Serratia marcescens* and Its Effect on Plasma Proteins," *J. Biochem.*, 104:616-621, (1988).

Molla, A., et al., "Degradation of Protease Inhibitors, Immunoglobulins, and Other Serum Proteins by *Serratia* Protease and Its Toxicity to Fibroblasts in Culture," *Infection and Immununity*, 53:522-529, (1986).
Oshida, T., et al., "A *Staphylococcus aureus* Autolysin That Has an N-Acetylmuramoyl-L-Alanine Amidase Domain and an Endo-β-N-Acetylglucosaminidase Domain: Cloning, Sequence, Analysis, and Characterization," *Proc. Natl. Acad. Sci. USA*, 92:285-289, (1995).
Rice, K., et al., "Description of *Staphylococcus* Serine Protease (*ssp*) Operon in *Staphylococcus aureus* and Nonpolar Inactivation of *sspA*-Encoded Serine Protease," *Infection and Immunity*, 69:159-169, (2001).
Rosenstein, R. and Götz, F., "Staphylococcal Lipases: Biochemical and Molecular Characterization," *Biochimie* 82:1005-1014, (2000).
Salamone, P.R. and Wodzinski, R.J., "Production, Purification and Characterization of a 50-kDa Extracellular Metalloprotease From *Serratia marcescens*," *Appl. Microbiol. Biotechnol.*, 48:317-324, (1997).
Shikata, S., et al., "Detection of Large COOH-Terminal Domains Processed From the Precursor of *Serratia marcescens* Serine Protease in the Outer Membrane of *Escherichia coli*," *J. Biochem.*, 111:627-632, (1992).
Sugai, M., et al., "Identification of Endo-β-N-Acetylglucosaminidase and N-Acetylmuramyl-L-Alanine Amidase as Cluster-Dispersing Enzymes in *Staphylococcus aureus*," *J. Bacteriol.*, 177:1491-1496, (1995).
van Kampen, M.D., et al., "Modifying the Substrate Specificity of Staphylococcal Lipases," *Biochem.*, 38:9524-9532, (1999).
Zahner, D. and Hakenbeck, R., "The *Streptococcus pneumoniae* Beta-Galactosidase Is a Surface Protein," *J. Bacteriol.*, 182:5919-5921, (2000).
Zhong, W. and Benkovic, S.J. "Development of an Internally Quenched Fluorescent Substrate for *Escherichia coli* Leader Peptidase," *Analytical Biochemistry*, 255:66-73 (1998).
O'Riordan, M., et al., "*Listeria* Intracellular Growth and Virulence Require Host-Derived Lipoic Acid," *Science*, 302:462-464 (2003).
Glaser, P., et al., "Comparative Genomics of *Listeria* Species," *Science*, 294:849-852 (2001).
Okuno, K., et al., "An Analysis of Target Preferences of *Excherichia coli* Outer-Membrane Endoportease OmpT for Use in Therapeutic Peptide Production: Efficient Cleavage of Substrates with Basic Amino Acids at the P4 and P6 Positions," *Biotechnol. Appl. Biochem.*, 36:77-84 (2002).
Cormican, M.G., et al., "Detection of Extended-Spectrum β-Lactamase (ESBL)-Producing Strains by the Etest ESBL Screen," *J. Clinical Microbiology* 34(8): 1880-1884, (1996).
Engels, W., "Secretion of staphylocoagulase be *Staphylococcus aureus*: the role of a cell-bound intermediate," *Antonie Van Leeuwenhoek* 47(6): 509-524, (1981).
Hadziyannis, E., et al., "Screening and confirmatory testing for extended spectrum β-lactamases (ESBL) in *Escherichia coli, Klebsiella pneumoniae* and *Klebsiella oxytoca* clinical isolates," *Diagnostic Microbiology and Infectious Disease*, 36:113-117, (2000).
McAleese, F.M., et al., "Loss of Clumping Factor B Fibrinogen Binding Activity by *Staphylococcus aureus* Involves Cessation of Transcription, Shedding and Cleavage by Metallaprotease," *J. Bio. Chem.* 276(32): 29969-29978, (2001).
Piorunska-Stolzmann, M., et al., "Serum glycerol ester hydrolase activity is related to zinc and copper concentrations in atherosclerosis obliterans and aneurysm," *J. Trace Elem. Med. Biol.* 12(1): 39-43, (1998).
Püutsep, K., et al., "Germ-free and Colonized Mice Generate the Same Products from Enteric Prodefensins," *J. Bio. Chem.* 275(51): 40478-40482, (2000).
Ton-That, H., et al., "Anchor Structure of Staphylococcal Surface Proteins," *J. Bio. Chem.*, 273(44): 29143-29149, (1998).
BBC New, Health, "Smart bandage 'spots infection'," [online] Nov. 5, 2001 [retrieved on Dec. 28, 2004] Retrieved from the Internet <URL:http://news.bbc.co.uk/1/hi/health/1634639.stm.
Janda, J.M. et al., "Overview of the Etiology of Wound Infections with Particular Emphasis on Community-Acquired Illnesses," *Eur. J. Clin. Microbiol. Infect. Dis.*, 16: 189-201 (1997).

(56) References Cited

OTHER PUBLICATIONS

English Translation of Japanese Office Action dated Oct. 1, 2008 from Japanese Patent Application 2003-563395 filed Sep. 29, 2008.
Communication pursuant to Article 94(3) EPC dated Oct. 9, 2008 cited in European Patent Application No. 03 708 910.6 filed Jan. 31, 2003.
Chronic Wound Care, 4th Ed., 2007, p. 123, Chapter 13, "Wound Assessment and Documentation."
Communication of Canadian Office Action dated Mar. 24, 2010 from Canadian Application 2,474,458.
Silletti, R.P., et al., "Microbiologic and Clinical Value of Primary Broth Cultures of Wound Specimens Collected with Swabs," J. Clin. Microbiol. 35(8): 2003-2006 (1997).
Smeltzer, M.S., et al., "Quantitative Spectrophotometric Assay for Staphylococcal Lipase," App. Environ. Microbiol. 58(9): 2815-2819 (1992).
Beliveau, C., et al., "Cloning, Sequencing, and Expression in Escherichia coli of a Streptococcus faecalis Autolysin," J. Bacteriology 173(18): 5619-5623 (1991).
Wolf, G.A., and Wirth, S.J., Soluble, Dye-Labelled Substrates for a Micro-Plate Assay of Proteinase Activity, J. Microbiol. Meth. 25: 337-342 (1996).
Wang, G., et al., "Solid-Phase Synthesis of Peptide Vinyl Sulfones as Potential Inhibitors and Activity-Based Probes of Cysteine Protease," Org. Ltrs 5(5): 737-740 (2003).
Holliday, M.G., et al., "Rapid Identification of Staphylococcus aureus by Using Fluorescent Staphylocoagulase Assays," 37(4): 1190-1192 (1999).
Lukomski S, et al., "Genetic Inactivation of an Extracellular Cysteine Protease (SpeB) Expressed by Streptococcus pyogenes Decreases Resistance to Phagocytosis and Dissemination to Organs," Infection and Immunity 66(2): 771-776 (1998).
Shaw L, et al., "The role and regulation of the extracellular proteases of Staphylococcus aureus," Microbiology 150: 217-28 (2004).
Cowell BA, et al., "Mutation of lasA and lasB reduces Pseudomonas aeruginosa invasion of epithelial cells," Microbiology, 149: 2291-99 (2003).
Ashbaugh CD, Wessels MR. "Absence of a cysteine protease effect on bacterial virulence in two murine models of human invasive group A streptococcal infection," Infection and Immunity, 69(11): 6683-6688 (2001).
Lukomski S., et al., "Inactivation of Streptococcus pyogenes extracellular cysteine protease significantly decreases mouse lethality of serotype M3 and M49 strains," J Clin Invest, 99(11): 2574-2580 (1997).
English Translation of Japanese Office Action dated Apr. 13, 2010 from Japanese Patent Application 2003-563395.
Communication pursuant to Article 94(3) EPC dated Apr. 21, 2010 cited in European Patent Application No. 03 708 940.6.
Communication pursuant to Article 94(3) EPC dated Aug. 17, 2009 cited in European Patent Application No. 03 708 940.6.
Communication pursuant to Article 94(3) EPC dated Mar. 2, 2009 cited in European Patent Application No. 03 708 940.6.
Communication pursuant to Article 94(3) EPC dated May 16, 2008 cited in European Patent Application No. 03 708 940.6.
Bauters, et al. "Enzymatic Differentiation of Candida parapsilosis from other Candida ssp. in a Membrane Filtration Test," J. Microbiol. Meth., 53: 11-15 (2003).
Bendjennat, M., et al., "Purification and Characterization of Mycoplasma penetrans Ca2+/Mg2+ Dependent Endonuclease," J. Bacteriology, 179: 2210-2220 (1997).
Bowie, J.U., et al., "Deciphering the message in protein sequences: tolerance to amino acid substitutions," Science, 247(4948): 1306-1310 (1990).
Chan, P.F. and Foster, S.J., "Role of SarA in virulence determinant production and environmental signal transduction in Staphylococcus aureus," Journal of Bacteriology, 180(23): 6232-6241 (1998).
Cunningham, B.C., and Wells, J.A., "High-resolution epitope mapping of hGH-receptor interactions by alanine-scanning mutagenesis," Science, 244(4908): 1081-1085 (1989).
Fallon, et al., "Role of Aspartic Proteasees in Disseminated Candida albicans Infection in Mice," Infection and Immunity, 65(2): 551-556 (1997).
PCT Application No. PCT/US2008/081483: International Preliminary Report on Patentability mailed May 4, 2010.
Gibson, D.G., et al., "Complete Chemical Synthesis, Assembly, and Cloning of a Mycoplasma genitalium Genome," Science, 319(5867): 1215-1220 (2008).
Giraud, F. et al, "Biodegradation of Anthracene and Fluoranthene by Fungi Isolated from an Experimental Constructed Wetlands for Wastewater Treatment," Water Research, 35(17): 4126-4136 (2001).
Glass, et al., Uniprot Entry MCAP_0157 (Jan. 24, 2006). Cited in PCT/US2008/081483 International Search Report mailed Aug. 31, 2009.
Grant, S.K., "Development of Novel Assays for Proteolytic Enzymes Using Rhodamine-Based Fluorogenic Substrates," J. Biomol. Screen., 7(6): 531-540 (2002).
Griffith, E.M.C.A., et al., "N-polymethylenecarboxymaleimides—a new class of probes for membrane sulphydryl groups," Febs Lett., 134(2): 261-263 (1981).
Hasseman, J.J., et al. "Microbial Genomic DNA Aminoally Labeling for Microarrays," The Institute of Genomic Research Standard Operating Procedure #M009.
Kannan, T., "ADP-Ribosylating and Vacuolating Cytotoxin of Mycoplasma pneumoniae Represents Unique Virulence Determinant Among Bacterial Pathogens," PNAS, 103: 6724-6729 (2006).
Kordula, T., et al., "Isolation and properties of stachyrase A, a chymotrypsin-like serine proteinase from Stachybotrys chartarum," Infection and Immunity, 70(1): 419-421 (2002).
Lowther, W.T., et al., "Engineering the Substrate Specificity of Rhizopuspepsin: The Role of Asp 77 of Fungal Aspartic Proteinases in Facilitating the Cleavage of Oligopeptide Substrates with Lysine in $P_1$," Protein Science, 4: 689-702 (1995).
Marcus, P.I., et al., "Mycoplasmas Produce Double-Stranded Ribonuclease," J. Cell Physiol., 143(3): 416-419 (1990).
McGarrity, G.J., et al., "Adenosine Phosphorylase-Mediated Nucleoside Toxicity. Application Towards the Dectection of Mycoplasmal Infection in Mammalian Cell Cultures," Exp. Cell Res., 139(1): 199-2005 (1982).
Minion, C., et al., "Identification and Preliminary Characterization of External Membrane-Bound Nuclease Activities in Mycoplasma pulmonis," Infection and Immunity, 51(1): 352-354 (1986).
Minion, C., et al., "Membrane-Associated Nuclease Activities in Mycoplasmas," J. of Bacteriology, 175: 7842-7847 (1993).
Miyazaki, et al., "Plasma (1-3)-beta-D-glucan and Fungal Antigenemia in Patients with Candidemia, Aspergillosis, and Cryptococcosis," J. Clin. Microbiol., 33(12): 3115-3118 (1995).
NCBI Blast: MCAP_0157. [Performed Aug. 18, 2009 by using 3, 11, 17 http://blast.ncbi.nlm.nih.gov/Blast.cgi]. Cited in PCT/US2008/081483 International Search Report mailed Aug. 31, 2009.
Obayashi, et al., "Pasma (1-3)-beta-D-glucan Measurement in Diagnosis of Invasive Deep Mycosis and Fungal Febrile Epsiodes," Lancet, 345: 17-20 (1995).
Orren, D.K. & Sancar, A., "The (A)BC Excinuclease of Escherichia coli has only the UvrB and UvrC Subunits in the Incision Complex," Proc. Natl. Soc. USA, 86(14): 5237-5241 (1989).
Polacheck, I. et al., "Distribution of Auto Lysins in Hyphae of Asperigillus-nidulans Evidence for a Lipid Mediated Attachment to Hyphal Walls," J. Bacteriology, 135(3): 741-747 (1978).
Ramalho, et al., "Characterization of Azo Reduction Activity in a Novel Ascomycete Yeast Strain," Applied Environmental Microbiology, 70(4): 2279-2288 (2004).
Rosenau, F. and Jaeger, K. "Bacterial lipases from Pseudomonas: regulation of gene expression and mechanisms of secretion" Biochimie 82(11):1023-32 (2000).
Safarik, "A Simple Method for Determination of Proteolytic Activity," Biotechnology Techniques, 1(2): 135-136 (1987).
Safarik, "An Inexpensive Insoluble Chromogenic Substrate for the Determination of Proteolytic Activitiy," J. Ind. Microbiol., 3: 259-261 (1988).
Schaffer, A.A., et al., "Improving the accuracy of PSI-BLAST protein database searches with composition-based statistics and other refinements," Nucleic Acids Res., 29(14): 2994-3005 (2001).

(56) References Cited

OTHER PUBLICATIONS

Starkenburg, "Thioredoxin-like Protein," Database EMBL [Online] EBI, Retrieved from the Internet on Oct. 11, 2005 at http://srs.ebi.ac.uk/srsbin/cgi-bin/wgetz, Database Accession No. Q3suq9$_{13}$ nitwn, 1Pg.

Vaginitis Definition; Retrieved from the Internet on Jan. 14, 2011 at http://www.mondofacto.com/facts/dictionary?vaginitis, 1 pg.

Valley, U., et al., "A Rapid Method for Detection of Mycoplasmas in Mammalian Cell Cultures and Comparison with Other Routine Techniques," Enzyme and Microbiol Technology, 17(5): 391-400 (1995).

Van Kampen, M.D., et al. "Cloning, purification and characterisation of *Staphylococcus warneri* lipase 2" Biochim Biophys Acta 1544 (1-2):229-41 (2001).

Wan, X., et al., "Identification and Initial Characterization of a Putative *Mycoplasma gallinarum* Leucine Aminopeptidase Gene," Curr. Microbiol., 48: 32-38 (2004).

Watanabe, T., "Proteolytic Activity of *Mycoplasma salivarium*," Adv. Dent. Res., 2(2): 297-300 (1988).

Watanabe, T., "Proteolytic Activity of Mycoplasmas and Ureaplasmas Isolated Freshly form Human Saliva," Medical Microbiology and Immunology, 173(5): 251-255 (1985).

Watanabe, T., et al., "Aminopeptidase and Caseinolytic Activities of *Mycoplasma salivarium*," Medical Microbiology and Immunlogy, 172(4): 257-264 (1984).

Wikipedia, http://en.wikipedia.org/wiki/Enzyme_assay#specific_activity, accessed on Aug. 2, 2010.

Zaugg, et al., "Secreted Aspartic Proteinase Family of *Candida tropicalis*," Infection and Immunity, 69(1): 405-412 (2001).

European Patent Application No. 03708940.6 Office Communicated dated Mar. 2, 2009.

European Patent Application No. 03708940.6 Office Communication dated Oct. 9, 2008.

European Patent Application No. 03708940.6 Office Communication dated May 16, 2008.

European Patent Application No. 03708940.6 Office Communication dated Apr. 21, 2010.

European Patent Application No. 03708940.6 Office Communication dated Aug. 17, 2009.

European Patent Application No. 03708940.6 Office Communication dated Dec. 16, 2010.

European Patent Application No. 03708940.6 European Search Report dated Feb. 21, 2006.

PCT Application No. PCT/US2003/03172: Notification of Transmittal of International Preliminary Examination Report dated Nov. 4, 2005.

PCT Application No. PCT/US2003/03172: Notification of Transmittal of International Search Report dated May 27, 2005.

PCT Application No. PCT/US2006/027240: International Preliminary Report on Patentability, Dated Jan. 16, 2008.

PCT Application No. PCT/US2006/027240: International Search Report, Dated Jan. 12, 2007.

PCT Application No. PCT/US2008/081483: International Search Report mailed Aug. 31, 2009.

Karlin, S., et al., "Applications and statistics for multiple high-scoring segments in molecular sequences," Proc. Natl. Acad. Sci. USA 90(12): 5873-5877 (1993).

English translation of Japanese Official Communication dated Jan. 11, 2013 in corresponding Japanese Patent Application No. 2011-165567 (3 pages).

Holliday et al: Rapid Identification of *Staphylococcus aureus* by Using Fluorescent Staphylocoagulase Assays Journal of Clinical Microbiology, Apr. 1999, p. 1990-1992.

\* cited by examiner

METHOD FOR DETECTING MICROORGANISMS

RELATED APPLICATIONS

This application is the U.S. National Stage of International Application No. PCT/US03/03172, filed Jan. 31, 2003, published in English, and claims priority under 35 U.S.C. §119 or 365 to U.S. Provisional Application Nos. 60/383,847 filed May 28, 2002 and 60/354,001 filed Jan. 31, 2002. The entire teachings of the above applications are incorporated herein by reference.

BACKGROUND OF THE INVENTION

Infection of wounds is a major source of healthcare expenditure in the United States. Approximately 5% of all surgical wounds become infected with microorganisms, and that figure is considerably higher (10-20%) for patients undergoing abdominal surgery. Bacterial species, such as Staphylococci are the most frequently isolated organisms from infected wounds. This is probably because humans are the natural reservoir for staphylococci in the environment, with up to 50% of the population colonized at any given time. Colonization rates are significantly higher in the hospital setting, both among healthcare workers, and among patients. Moreover, the colonizing organisms in the hospital environment are likely to be resistant to many forms of antimicrobial therapy, due to the strong selective pressure that exists in the nosocomial environment, where antibiotics are frequently used. Staphylococci are usually carried as harmless commensals, however given a breach in the epidermis, they can cause severe, even life threatening infection.

Staphylococci are the most common etiologic agents in surgical wound infections; others include, but are not limited to *Streptococcus pyogenes* (*S. pyogenes*), *Pseudomonas aeruginosa* (*P. aeruginosa*), *Enterococcus faecalis* (*E. faecalis*), *Proteus mirabilis* (*P. mirabilis*), *Serratia marcescens* (*S. marcescens*), *Enterobacter clocae* (*E. clocae*), *Acetinobacter anitratus* (*A. anitratus*), *Klebsiella pneumoniae* (*K. pneumonia*), and *Escherichia coli* (*E. coli*).

Post-surgical infection due to any of the above organisms is a significant concern of hospitals. The most common way of preventing such infection is to administer prophylactic antibiotic drugs. While generally effective, this strategy has the unintended effect of breeding resistant strains of bacteria. The routine use of prophylactic antibiotics should be discouraged for the very reason that it encourages the growth of resistant strains.

Rather than using routine prophylaxis, a better approach is to practice good wound management, i.e., keep the area free from bacteria before, during, and after surgery, and carefully monitor the site for infection during healing. Normal monitoring methods include close observation of the wound site for slow healing, signs of inflammation and pus, as well as measuring the patient's temperature for signs of fever. Unfortunately, many symptoms are only evident after the infection is already established. Furthermore, after a patient is discharged from the hospital they become responsible for monitoring their own healthcare, and the symptoms of infection may not be evident to the unskilled patient.

A system or biosensor that can detect the early stages of infection before symptoms develop would be advantageous to both patients and healthcare workers. If a patient can accurately monitor the condition of a wound after discharge from the hospital, then appropriate antimicrobial therapy can be initiated early enough to prevent a more serious infection.

SUMMARY OF THE INVENTION

It has been found that molecules, for example, proteins secreted by microorganisms, such as bacteria or fungi, expressed on the cell surface of microorganisms, or expressed on the surface of a cell infected with a virus or prion can serve as markers for the detection of the presence or absence of the microorganism in a sample, for example, a wound or body fluid. Accordingly, the present invention features a method of detecting the presence or absence of a microorganism in a sample by detecting the presence or absence of a molecular marker for the microorganism in the sample. In particular, the molecular markers to be detected include proteins, such as enzymes that are specific to a species of microorganism.

In one aspect, the invention features a method for detecting the presence or absence of a microorganism in a sample, comprising the steps of contacting the sample with a detectably labeled substrate for an enzyme produced and/or secreted by the microorganism, under conditions that result in modification of the substrate by the enzyme; and detecting the modification or the absence of the modification of the substrate. Modification of the substrate indicates the presence of the microorganism in the sample, and the absence of modification of the substrate indicates the absence of the microorganism in the sample. In particular, the substrate can consist of labeled peptide that is cleaved by a protease enzyme to give a signal that can be detected. Furthermore, this peptide can be designed with a particular sequence of amino acid residues extending from one end of the original substrate peptide as a "tag" for use in covalently coupling the substrate to a surface.

In another aspect, the present invention features a method for diagnosing the presence or absence of a wound infection in a subject, comprising the steps of a) contacting a sample obtained from a wound in a subject with a detectably labeled substrate for an enzyme produced and/or secreted by a microorganism, under conditions that result in modification of the substrate by the enzyme; and b) detecting a modification or the absence of a modification of the substrate. Modification of the substrate indicates the presence of a wound infection in the subject, and the absence of modification of the substrate indicates the absence of an infection in the subject.

In yet another aspect, the present invention features a method for diagnosing the presence or absence of a wound infection in a subject, comprising the steps of a) contacting a wound in a subject with a detectably labeled substrate for an enzyme produced and/or secreted by a microorganism, under conditions that result in modification of the substrate by the enzyme; and b) detecting a modification or the absence of a modification of the substrate. Modification of the substrate indicates the presence of a wound infection in the subject, and the absence of modification of the substrate indicates the absence of an infection in the subject.

In another aspect, the invention features a biosensor for detecting the presence or absence of a microorganism, for example, a wound-specific bacteria in a sample, comprising a solid support and a detectably labeled substrate for an enzyme produced and/or secreted by the microorganism, wherein the substrate is attached to the solid support.

In still another aspect, the present invention features a kit for detecting a wound infection, comprising a biosensor for detecting the presence or absence of a microorganism in a sample, and one or more reagents for detecting the presence of the microorganism that is the causative agent of the wound infection. For example, the reagent can be used to detect an enzyme secreted by the microorganism. In particular, the reagent can be used to detect the modification of the substrate of the biosensor.

In yet another aspect, the present invention features a polypeptide comprising or consisting of the sequence of SEQ ID NO: 1, 2, 3, 4, 5, 9, or 10. These polypeptides are useful for the identification and/or detection of the presence of wound-specific enzymes as described herein in a sample. In one embodiment, the polypeptide is detectably labeled.

In another aspect, the present invention features a nucleic acid comprising or consisting of the sequence of SEQ ID NO: 6, 7, or 8. This nucleic acid sequences are useful for the identification and/or detection of the presence of wound-specific enzymes as described herein in a sample. In one embodiment, the nucleic acid is detectably labeled.

DETAILED DESCRIPTION OF THE INVENTION

Figure 1:
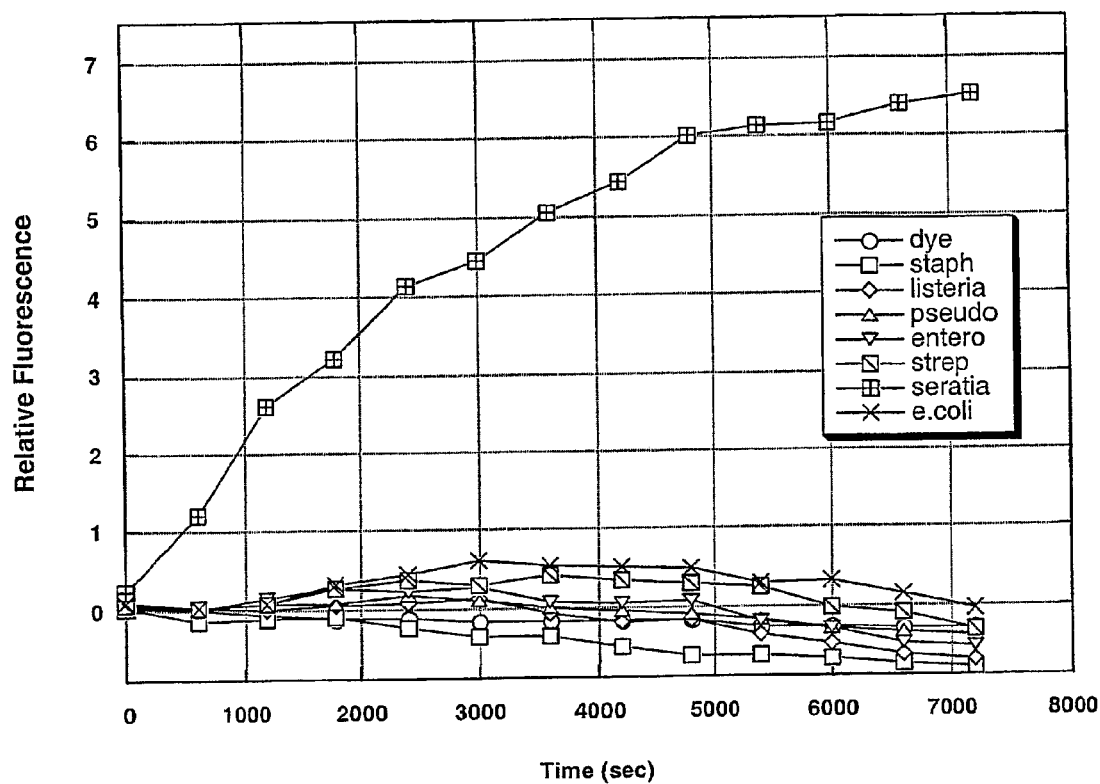
FIG. 1 is a graph of the cleavage of a target polypeptide substrate (relative fluorescence) over time (minutes) in samples containing an active bacterial culture or a water control, substrate, and reaction buffer. (staph=Staphylococcus aureus; listeria=Listeria monocytogenes; pseudo=Pseudomonas aeruginosa; entero=Enterococcus faecalis; strep=Streptococcus salivarius; Seratia=Serratia marcescens; e.coli=Escherichia coli)

As part of their normal growth processes, many microorganisms secrete a number of enzymes into their growth environment. These enzymes have numerous functions including, but not limited to, the release of nutrients, protection against host defenses, cell envelope synthesis (in bacteria) and/or maintenance, and others as yet undetermined. Many microorganisms also produce enzymes on their cell surface that are exposed to (and interact with) the extracellular environment. Many of these enzymes are specific to the microorganism that secretes them, and as such, can serve as specific markers for the presence of those microorganisms. A system that can detect the presence of these enzymes that are produced and/or secreted can equally serve to indicate the presence of the producing/secreting microorganism. Alternatively, a system that can detect the absence of these enzymes that are produced and/or secreted can equally serve to indicate the absence of the producing/secreting microorganism. Such a detection system is useful for detecting or diagnosing an infection, for example, a wound infection.

A microorganism detection test system, as described herein can be tailored to detect one specific microorganism by identifying a protein such as a secreted enzyme specific to the microorganism to be detected. Alternatively, a test system can be designed to simultaneously identify more than one microorganism species (for example, at least 2, at least 5, or at least 10 different microorganism species), such as those that commonly infect wounds. Identifying those enzymes that are common to certain classes of pathogenic microorganisms, but which are not present in non-pathogenic microorganisms is one way to achieve this goal. Such enzymes can be identified, for example, with a computer based bioinformatics screen of the microbial genomic databases. By using enzymes as the basis for detection systems, sensitive tests can be designed, since even a very small amount of enzyme can catalyze the turnover of a substantial amount of substrate.

The present invention pertains to the identification of bacterial proteins that are specific for microorganisms that are the causative agent of a wound, i.e., wound-specific. The proteins can be grouped into classes insofar as they represent targets for developing agents for detecting the bacteria that produce them and present them on the cell surface or that secrete them. As described herein, proteins were grouped into nine classes. The presence of a pathogenic bacterium can be detected by designing a synthetic substrate that will specifically react with an enzyme that is present on the surface of the cell or secreted. These synthetic substrates can be labeled with a detectable label such that under conditions wherein their respective enzymes specifically react with them, they undergo a modification, for example, a visible color change that is observed.

The enzymes that are used in the bacteria detection method of the present invention are preferably wound-specific enzymes. As used herein, a wound-specific enzyme is an enzyme produced and/or secreted by a pathogenic bacteria, but is not produced and/or secreted by a non-pathogenic bacteria. Examples of pathogenic bacteria include, but are not limited to *staphylococcus* (for example, *Staphylococcus aureus*, *Staphylococcus epidermidis*, or *Staphylococcus saprophyticus*), *streptococcus* (for example, *Streptococcus pyogenes*, *Streptococcus pneumoniae*, or *Streptococcus agalactiae*), *enterococcus* (for example, *Enterococcus faecalis*, or *Enterococcus faecium*), *corynebacteria* species (for example, *Corynebacterium diptheriae*), *bacillus* (for example, *Bacillus anthracis*), *listeria* (for example, *Listeria monocytogenes*), *Clostridium* species (for example, *Clostridium perfringens, Clostridium tetanus, Clostridium botulinum, Clostridium difficile*), *Neisseria* species (for example, *Neisseria meningitidis*, or *Neisseria gonorrhoeae*), *E. coli*, *Shigella* species, *Salmonella* species, *Yersinia* species (for example, *Yersinia pestis, Yersinia pseudotuberculosis*, or *Yersinia enterocolitica*), *Vibrio cholerae*, *Campylobacter* species (for example, *Campylobacter jejuni* or *Campylobacter fetus*), *Helicobacter pylori*, *pseudomonas* (for example, *Pseudomonas aeruginosa* or *Pseudomonas mallei*), *Haemophilus influenzae*, *Bordetella pertussis*, *Mycoplasma pneumoniae*, *Ureaplasma urealyticum*, *Legionella pneumo-*

*phila, Treponema pallidum, Leptospira interrogans, Borrelia burgdorferi*, mycobacteria (for example, *Mycobacterium tuberculosis*), *Mycobacterium leprae, Actinomyces* species, *Nocardia* species, *chlamydia* (for example, *Chlamydia psittaci, Chlamydia trachomatis,* or *Chlamydia pneumoniae*), *Rickettsia* (for example, *Rickettsia ricketsii, Rickettsia prowazekii* or *Rickettsia akari*), *brucella* (for example, *Brucella abortus, Brucella melitensis*, or *Brucella suis*), *Proteus mirabilis, Serratia marcescens, Enterobacter clocae, Acetinobacter anitratus, Klebsiella pneumoniae* and *Francisella tularensis*. Preferably, the wound-specific bacteria is *staphylococcus, streptococcus, enterococcus, bacillus, Clostridium* species, *E. coli, yersinia, pseudomonas, Proteus mirabilis, Serratia marcescens, Enterobacter clocae, Acetinobacter anitratus, Klebsiella pneumoniae* or *Mycobacterium leprae*. For example, the wound-specific enzyme can be produced and/or secreted by *Staphylococcus aureus, Staphylococcus epidermidis, Streptococcus pyogenes, Pseudomonas aeruginosa, Enterococcus faecalis, Proteus mirabilis, Serratia marcescens, Enterobacter clocae, Acetinobacter anitratus, Klebsiella pneumoniae* and/or *Escherichia coli*.

The wound-specific enzyme may be a lysin (an enzyme that functions to lyse host cells); a cell wall enzyme (an enzyme involved in the synthesis and turnover of bacterial cell wall components, including peptidoglycan), a protease (an enzyme that specifically or non-specifically cleaves a peptide, polypeptide, or protein), a hydrolase (an enzyme that breaks down polymeric molecules into their subunits), a metabolic enzyme (an enzyme designed to perform various housekeeping functions of the cell, such as breaking down nutrients into components that are useful to the cell), or a virulence enzyme (an enzyme that is required by the bacterial cell to cause an infection).

Preferably, the enzyme is one or more of the following (the GenBank Accession Number and/or name of an example of each protein is provided in parentheses): autolysin (Atl), FemB protein (femB), fmhA protein (fmhA), TcaB protein (tcaB), enterotoxin P (sep), exotoxin 6 (set6), exotoxin 7 (set7), exotoxin 8 (set8), exotoxin 9 (set9), exotoxin 10 (set10), exotoxin 11 (set11), exotoxin 12 (set12), exotoxin 13 (set13), exotoxin 14 (set14), exotoxin 15 (set15), Clumping factor B (clfB), Blt-like protein (SA1269), FmhC protein (fmhC(eprh)), enterotoxin SEM (sem), enterotoxin SeN (sen), enterotoxin SeO (seo), leukotoxin LukE (lukE), truncated integrase (SA0356), enterotoxin typeC3 (sec3), enterotoxin Yent1 (yent1), enterotoxin YENT2 (yent2), glycerol ester hydrolase (geh), immunodominant antigen A (isaA), serine protease SplB (splB), serine protease SplC (splC), ABC transporter permease (vraG), phosphomevalonate kinase (mvaK2), gamma-hemolysin component B (hlgB), gamma-hemolysin component C (hlgC), tagatose-6-phosphate kinase (lacC), cysteine protease precursor (sspB), 6-phospho-beta-galactosidase (lacG), extracellular enterotoxin L (sel), triacylglycerol lipase precursor (lip), Staphopain, Cysteine Proteinase (SA1725), tagatose 1,6-diphosphate aldolase (lacD), gamma-hemolysin chain II precursor (hlgA), enterotoxin homolog (SA1429), mannitol-1-phosphate 5-dehydrogenase (mtlD), staphylococcal accessory regulator A (sarA), lactose phosphotransferase system repressor (lacR), capsular polysaccharide biosynthesis (SA2457), capA, galactose-6-phosphate isomerase LacA subunit (lacA), fibrinogen-binding protein A, clumping factor (clfA), extracellular enterotoxin type G precursor (seg), extracellular enterotoxin type I precursor (sei), leukotoxin, LukD [Pathogenicity island SaPIn3] (lukD), fibronectin-binding protein homolog (fnb), fibronectin-binding protein homolog (fnbB), holin homolog [Bacteriophage phiN315] (SA1760), similar to D-xylulose reductase (SA2191), secretory antigen precursor SsaA homolog (ssaA), factor essential for expression of methicillin resistance (femA), similar to exotoxin 2 (SA0357), similar to exotoxin 1 (SA1009), similar to exotoxin 4 (SA1010), similar to exotoxin 3 (SA1011), staphylococcal accessory regulator A homolog (sarH3), similar to transaldolase (SA1599), similar to 5-nucleotidase (SA0022), undecaprenyl-PP-MurNAc-pentapeptide-UD-PGlcNAc GlcNAc transferase (murG), similar to exonuclease SbcD (SA1180), similar to membrane protein (SA2148), Ser-Asp rich fibrinogen-binding, bone sialoprotein-binding protein (sdrC), Ser-Asp rich fibrinogen-binding, bone sialoprotein-binding protein (sdrD), Ser-Asp rich fibrinogen-binding, bone sialoprotein-binding protein (sdrE), similar to oligoendopeptidase (SA1216), similar to MHC class II analog (SA2006), similar to transcription factor (SA0858), probable beta-lactamase [Pathogenicity island SaPIn3] (SA1633), similar to NA(+)/H(+) exchanger (SA2228), similar to xylitol dehydrogenase (SA0242), similar to cell wall enzyme EbsB (SA1266), similar to transposase for IS232 (SAS069), similar to transposase for IS232 (SAS070), similar to transport protein SgaT (SA0318), similar to transcription regulator (SA0187), similar to ribose transporter RbsU (SA0260), similar to regulatory protein PfoR (SA0298), similar to enterotoxin A precursor (SA1430), similar to regulatory protein pfoR (SA2320), transposase homolog for IS232 [Pathogenicity island SaPIn3] (tnp), similar to formate transporter NirC (SA0293), similar to D-octopine dehydrogenase (SA2095), similar to rbs operon repressor RbsR (SA0261), similar to cell surface protein Map-w (SA0841), similar to fibrinogen-binding protein (SA1000), similar to fibrinogen-binding protein (SA1003), similar to fibrinogen-binding protein (SA1004), similar to staphylocoagulase precursor (SA0743), similar to ferrichrome ABC transporter (SA0980), similar to peptide binding protein OppA (SA0849), similar to proton antiporter efflux pump (SA0263), similar to kdp operon sensor protein (kdpD(SCCmec)), similar to secretory antigen precursor SsaA (SA0270), similar to outer membrane protein precursor (SA0295), similar to deoxyribodipyrimidine photolyase (SA0646), similar to secretory antigen precursor SsaA (SA2097), similar to integral membrane efflux protein (SA2233), similar to secretory antigen precursor SsaA (SA2332), similar to secretory antigen precursor SsaA (SA2353), similar to transmembrane efflux protein (SA0099), similar to multi-drug resistance efflux pump (SA0115), probable specificity determinant HsdS [Pathogenicity island SaPIn3] (SA1625), similar to ABC transporter ATP-binding protein (SA0339), similar to cobalamin synthesis related protein (SA0642), similar to transcription regulator MarR family (SA2060), similar to N-Carbamoylsarcosine Amidohydrolase (SA2438), similar to teichoic acid biosynthesis protein B (SA0243), similar to teichoic acid biosynthesis protein B (SA0247), similar to transcription regulator, RpiR family (SA2108), similar to two component sensor histidine kinase (SA2180), similar to succinyl-diaminopimelate desuccinylase (SA1814), similar to extracellular matrix and plasma binding (SA0745), similar to transcription antiterminator BglG family (SA1961), similar to cobalamin synthesis related protein CobW (SA2368), similar to DNA polymerase III, alpha chain PolC type (SA1710), similar to spermine/spermidine acetyltransferase blt (SA1931), similar to trimethylamine dehydrogenase (EC 1.5.99.7) (SA0311), similar to AraC/XylS family transcriptional regulator (SA0622), similar to PTS fructose-specific enzyme IIBC component (SA0320), similar to beta-lactamase [Pathogenicity island SaPIn1] (SA1818), similar to 4-diphosphocytidyl- 2C-methyl-D-erythritol synthase (SA0241), similar to synergohymenotropic toxin precursor—*Staphylococcus intermedius* (SA1812), similar to bacteriophage terminase small subunit [Pathogenicity island SaPIn1] (SA1820), similar to poly (glycerol-phosphate) alpha-glucosyltransferase (teichoic acid biosynthesis)(SA0523). The above referenced GenBank Accession Numbers are those corresponding to *Staphylococcus aureus* proteins. The GenBank Accession Numbers for these proteins from other species are available to one skilled in the art. Such GenBank Accession Numbers can be obtained, for example, by searching the GenBank protein database by the desired protein and species name. Alternatively, the *Staphylococcus aureus* protein sequence can be obtained using the provided GenBank Accession number and/or protein name, and this sequence can be searched for proteins from other species with similar sequence identity or homology, for example, using the BLAST program described herein. Protein sequences from other species can then be obtained from the search results.

Substrates for use in the present invention include any molecule, either synthetic or naturally-occurring that can interact with an enzyme of the present invention. Examples of substrates include those substrates described herein, as well as substrates for these enzymes that are known in the art. Other examples of substrates include Alt derived fluorescent peptides, for example, PGTKLYTVPW-pyrene (SEQ ID NO: 1) (which can bind to the surface of *Staphylococcus*; it is predicted that an increase in fluorescence upon binding would occur); fluorescent peptidoglycans, for example, flourescent-N-acetylglucosamine-[b-1,4-N acetylmuramic acid, fluorescent-N-acetylmuramyl-L-alanine, or fluorescent-lipoteichoic acid (peptidoglycans over-labeled with fluorescein would be quenched from fluorescing, but following hydrolysis by a wound pathogen would fluoresce); and a lipid vesicle containing dye for the detection of hemolysin (many hemolysins form ordered protein complexes that are pore forming toxins, and can be detected by the release of dye from a lipid vesicle followed by diffusion of the dye onto a hydrophobic solid substrate). Such substrates described herein can be obtained from commercial sources, e.g., Sigma (St. Louis, Mo.), or can be produced, e.g., isolated or purified, or synthesized using methods known to those of skill in the art.

The enzymes of the present invention can modify substrates, for example, proteins or polypeptides by cleavage, and such modification can be detected to determine the presence or absence of a pathogen in a sample. One method for detecting modification of a substrate by an enzyme is to label the substrate with two different dyes, where one serves to quench the fluorescence of the other dye by fluorescence energy transfer (FRET) when the molecules, for example, dyes or colorimetric substances are in close proximity, and is measured by detecting changes in fluorescence.

FRET is the process of a distance-dependent excited state interaction in which the emission of one fluorescent molecule is coupled to the excitation of another. A typical acceptor and donor pair for resonance energy transfer consists of 4-[[-(dimethylamino)phenyl]azo] benzoic acid (DABCYL, Dabcyl) and 5-[(2-aminoethylamino] naphthalene sulfonic acid (EDANS, Edans). EDANS is excited by illumination with 336 nm light, and emits a photon with wavelength 490 nm. If a DABCYL moiety is located within 20 angstroms of the EDANS, this photon will be efficiently absorbed. DABCYL and EDANS will be attached to opposite ends of a peptide substrate. If the substrate is intact, FRET will be very efficient. If the peptide has been cleaved by an enzyme, the two dyes will no longer be in close proximity and FRET will be inefficient. The cleavage reaction can be followed by observing either a decrease in the fluorescence of the acceptor or an increases in fluorescence of the donor. An increase in fluorescence of EDANS can be measured at, for example, 485 nm or 538 nm.

If the substrate to be modified is a protein, peptide, or polypeptide, the substrate can be produced using standard recombinant protein techniques (see for example, Ausubel et al., "Current Protocols in Molecular Biology," John Wiley & Sons, (1998), the entire teachings of which are incorporated by reference herein). In addition, the enzymes of the present invention can also be generated using recombinant techniques. Through an ample supply of enzyme or its substrate, the exact site of modification can be determined, and a more specific substrate of the enzyme can be defined, if so desired. This substrate can also be used to assay for the presence of the pathogenic bacteria.

The substrates are labeled with a detectable label that is used to monitor interactions between the enzyme and the substrate and detect any substrate modifications, for example, cleavage of the substrate or label resulting from such interactions. Examples of detectable labels include various dyes that can be incorporated into substrates, for example, those described herein, spin labels, antigen or epitope tags, haptens, enzyme labels, prosthetic groups, fluorescent materials, chemiluminescent materials, bioluminescent materials, and radioactive materials. Examples of suitable enzyme labels include horseradish peroxidase, alkaline phosphatase, β-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a chemiluminescent material includes luminol; examples of bioluminescent materials include luciferase, luciferin, and aequorin, and examples of suitable radioactive material include $^{125}I$, $^{131}I$, $^{35}S$, and $^3H$. Other examples of detectable labels include Bodipy, Pyrene, Texas Red, IAEDANS, Dansyl Aziridine, IATR and fluorescein. Succimidyl esters, isothiocyanates, and iodoacetamides of these labels are also commercially available. When detectable labels are not employed, enzymatic activity can be determined by other suitable methods, for example detection of substrate cleavage through electrophoretic analysis, or other methods known to one skilled in the art.

One example of a preferred detectable label is a chromogenic dye that allows monitoring of the hydrolysis of the substrate by the bacterial enzyme. An example of such a dye is para-nitrophenol. When conjugated to a substrate molecule, this dye will remain colorless until the substrate is modified by the secreted enzyme, at which point it turns yellow. The progress of the enzyme-substrate interaction can be monitored by measuring absorbance at 415 nm in a spectrophotometer. Other dyes that produce detectable modification, e.g., a visible color change, are known to those of skill in the art.

The sample in which the presence or absence of bacteria is detected, or a wound infection is diagnosed, can be, for example, a wound, a body fluid, such as blood, urine, sputum, or wound fluid (for example, pus produced at a wound site). The sample can also be any article that bacteria may be contained on/in, for example, a wound dressing, a catheter, a urine collection bag, a blood collection bag, a plasma collection bag, a polymer, a disk, a scope, a filter, a lens, foam, cloth, paper, a suture, swab, test tube, a well of a microplate, contact lens solutions, or a swab from an area of a room or building, for example, an examination room or operating room of a healthcare facility, a bathroom, a kitchen, or a process or manufacturing facility.

The present invention also features a biosensor for detecting a (one or more, for example, at least 2, at least 5, at least 10, at least 20, at least 30, at least 50, at least 75, or at least 100) marker protein enzyme(s) described herein and for notifying a consumer of the presence of the marker protein. As used herein, a "biosensor" is a device that incorporates one or more of the above-described substrates, or other substrates described herein, and produces a detectable signal upon sensing the presence or absence of bacteria. A biosensor for use in healthcare settings or home-use to detect infected wounds comprising a (one or more) specific substrate(s) that is coupled to a solid support that is proximal to a wound or other body fluid that is being monitored for bacterial contamination is provided. Preferably, the substrate is covalently bound to a label and thus has a detection signal that upon proteolysis of the substrate-label bond indicates the presence of the bacteria.

The biosensor is made by first determining the specific substrate of a specific enzyme characteristic of the bacteria to be detected. The determined specific substrate is labeled with one or more, and preferably, a plurality of detectable labels, for example, chromatogenic or fluorescent leaving groups. Most preferably, the labeling group provides a latent signal that is activated only when the signal is proteolytically detached from the substrate. Chromatogenic leaving groups include, for example, para-nitroanalide groups. Should the substrate come into contact with an enzyme secreted into a wound or other body fluid by bacteria or presented on the surface of a bacterial cell, the enzyme modifies the substrates in a manner that results in detection of such a modification, for example, a change in absorbance, which can be detected visually as a change in color (for example, on the solid support, such as a wound dressing), or using spectrophotometric techniques standard in the art.

The biosensor of the present invention also can comprise one or more substrates (for example, at least 2, at least 5, at least 10, at least 20, at least 30, at least 50, at least 75, or at least 100 substrates) for produced and/or secreted enzymes of pathogenic bacteria. The biosensor is a solid support, for example, a wound dressing (such as a bandage, or gauze), any material that needs to be sterile or free of microbial contamination, for example, a polymer, disk, scope, filter, lens, foam, cloth, paper, or sutures, or an article that contains or collects the sample (such as a urine collection bag, blood or plasma collection bag, test tube, catheter, swab, or well of a microplate).

Typically, the solid support is made from materials suitable for sterilization if the support directly contacts the wound or sample. In one embodiment of the present invention, the biosensor can be directly contacted with the wound. In some instances, a sterile covering or layer is used to prevent contamination of the wound or body fluid upon such direct contact. If such sterile coverings are used, they will have properties that make them suitable for sterilization, yet do not interfere with the enzyme/substrate interaction. Preferably, the portion of the biosensor that comes into contact with the wound is also nonadherent to permit easy removal of the biosensor from the sample surface. For example, if the biosensor comprises a wound dressing, the dressing contacts the wound for a time sufficient for the enzyme substrate to react and then the dressing is removed from the wound without causing further damage to the wound or surrounding tissue.

Substrates suitably labeled with detectable labels, for example, a chromogenic dye, and attached or incorporated into a sensor apparatus, can act as indicators of the presence or absence of pathogenic bacteria that secrete the aforementioned enzymes. When more than one substrate is utilized, each may be labeled so as to distinguish it from another (for example, using different detectable labels) and/or each may be localized in a particular region on the solid support.

Substrates with hydrophobic leaving groups can be non-covalently bound to hydrophobic surfaces. Alternatively hydrophilic or hydrophobic substrates can be coupled to surfaces by disulfide or primary amine, carboxyl or hydroxyl groups. Methods for coupling substrates to a solid support are known in the art. For example, fluorescent and chromogenic substrates can be coupled to solid substrates using non-essential reactive termini such as free amines, carboxylic acids or SH groups that do not effect the reaction with the wound pathogens. Free amines can be coupled to carboxyl groups on the substrate using, for example, a 10 fold molar excess of either N-ethyl-N'-(3-dimethylaminopropyl)carbodiimide hydrochloride (EDC) or N-cyclohexyl-N'-2-(4'-methyl-morpholinium) ethyl carbodiimide-p-toluene sulphonate (CMC) for 2 hrs at 4° C. in distilled water adjusted to pH 4.5 to stimulate the condensation reaction to form a peptide linkage. SH groups can be reduced with DTT or TCEP and then coupled to a free amino group on a surface with N-e-Male-imidocaproic acid (EMCA, Griffith et al., Febs Lett. 134: 261-263, 1981).

One example of a substrate for use in the present invention is a polypeptide comprising or consisting of the amino acid sequence of SEQ ID NO: 1, 2, 3, 4, 5, 9, or 10, or a polypeptide having at least 50%, 60%, 70%, 80%, 85%, 90%, 95%, or 99% sequence identity to SEQ ID NO: 1, 2, 3, 4, 5, 9, or 10, as determined using a sequence comparison program and parameters described herein. Such polypeptides are enzymatically cleaved by wound specific proteases as described herein.

Another example of a substrate for use in the present invention is a polypeptide comprising or consisting of the nucleic acid sequence of SEQ ID NO: 6, 7, or 8, or a nucleic acid sequence having at least 50%, 60%, 70%, 80%, 85%, 90%, 95%, or 99% sequence identity to SEQ ID NO: 6, 7, or 8, as determined using a sequence comparison program and parameters described herein. Such polypeptides are enzymatically cleaved by wound specific proteases as described herein.

The polypeptides of the invention also encompass fragments and sequence variants of the polypeptides and nucleic acids described above. Variants include a substantially homologous polypeptide encoded by the same genetic locus in an organism, i.e., an allelic variant, as well as other variants. Nucleic acid variants also include allelic variants. Variants also encompass polypeptides or nucleic acids derived from other genetic loci in an organism, but having substantial homology to a polypeptide of SEQ ID NO: 1, 2, 3, 4, 5, 9, or 10 or a nucleic acid of SEQ ID NO: 6, 7, or 8. Variants also include polypeptides or nucleic acids substantially homologous or identical to these polypeptides or nucleic acids but derived from another organism, i.e., an ortholog. Variants also include polypeptides or nucleic acids that are substantially homologous or identical to these polypeptides or nucleic acids that are produced by chemical synthesis. Variants also include polypeptides or nucleic acids that are substantially homologous or identical to these polypeptides or nucleic acids that are produced by recombinant methods.

The percent identity of two amino acid sequences or two nucleic acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions× 100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., Proc. Natl. Acad. Sci. USA, 90:5873-5877, 1993). Such an algorithm is incorporated into the BLAST programs (version 2.2) as described in Schaffer et al. (Nucleic Acids Res., 29:2994-3005, 2001). When utilizing BLAST and Gapped BLAST programs, the default parameters of the respective programs can be used. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences or two nucleic acid sequences can be accomplished using the GAP program in the GCG software package (Accelrys Inc., San Diego, Calif.) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be accomplished using the GAP program in the GCG software package (Accelrys Inc.), using a gap weight of 50 and a length weight of 3.

Other preferred sequence comparison methods are described herein.

The invention also encompasses polypeptides having a lower degree of identity but having sufficient similarity so as to perform one or more of the same functions performed by the polypeptide, e.g., the ability to act as a substrate for a *Serratia marcescens* specific protease. Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., Science 247: 1306-1310, 1990).

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region, such critical regions include the cleavage site for a *Serratia marcescens* specific protease.

Amino acids in a polypeptide of the present invention that are essential for cleavage by a *Serratia marcescens* specific protease can be identified by methods known in the art, such as site-directed mutagenesis or alanine-scanning mutagenesis (Cunningham et al., Science, 244: 1081-1085, 1989). The latter procedure introduces a single alanine mutation at each of the residues in the molecule (one mutation per molecule).

The invention also includes polypeptide fragments of the amino acid sequence of SEQ ID NO: 1, 2, 3, 4, 5, 9, or 10 or the nucleic acid sequence of SEQ ID NO: 6, 7, or 8 or functional variants thereof. Fragments can be derived from a polypeptide comprising SEQ ID NO: 1, 2, 3, 4, 5, 9, or 10 or a nucleic acid comprising SEQ ID NO: 6, 7, or 8. The present invention also encompasses fragments of the variants of the polypeptides and nucleic acids described herein. Useful fragments include those that retain the ability to act as substrates for a wound specific protease.

Fragments can be discrete (not fused to other amino acids or polypeptides) or can be within a larger polypeptide. Further, several fragments can be comprised within a single larger polypeptide. In one embodiment a fragment designed for expression in a host can have heterologous pre- and pro-polypeptide regions fused to the amino terminus of the polypeptide fragment and an additional region fused to the carboxyl terminus of the fragment.

The biosensors of the present invention can be used in any situation where it is desirable to detect the presence or absence of bacteria, and in particular, pathogenic bacteria. For example, bacteria that collects on work surfaces in health care facilities, and in particular in operating rooms can be detected with a biosensor as described herein. A substrate, or more than one substrate, that can be modified by an enzyme secreted by or presented on the surface of a bacteria is labeled and covalently bound to a collector substrate, such as cotton fibers on the tip of a swab. When more than one substrate is utilized, each may be labeled so as to distinguish it from another (for example, using different detectable labels) and/ or each may be localized in a particular region on the solid support. The swab tip is used to wipe the surface suspected of being contaminated by bacteria. The swab tip is placed in a medium and incubated using conditions that allow modification of the labeled substrate if an enzyme specific for the bound, labeled substrate(s) is present.

The present invention also features a kit for detecting wound-specific bacteria as described herein. The kit can comprise a solid support, for example, having a plurality of wells (e.g., a microtiter plate), to which a detectably labeled substrate is linked, coupled, or attached. A means for providing one or more buffer solutions is provided. A negative control and/or a positive control can also be provided. Suitable controls can easily be derived by one of skill in the art. A sample suspected of being contaminated by a pathogen described herein is prepared using the buffer solution(s). An aliquot of the sample, negative control, and positive control is placed in its own well and allowed to react. Those wells where modification of the substrate, for example, a color change is observed are determined to contain a microbial pathogen. Such a kit is particularly useful for detecting a wound infection in a subject.

Also encompassed by the present invention is a kit that comprises a biosensor, such as a packaged sterilized wound dressing, and any additional reagents necessary to perform the detection assay.

The method and/or biosensor of the present invention can be used to detect the presence or absence of any wound-specific enzyme described herein. For example, the method and/or biosensors can be used to detect the presence or absence of lipase enzymes secreted by pathogenic bacteria. It has been discovered that certain bacteria secrete lipases into their environment as part of their survival and/or virulence mechanisms. The lipases serve to break down lipids in the growth environment in order to release nutrients. Lipases may also play a role in disarming mammalian host defenses during infection. Synthetic substrates for these secreted enzymes can be employed to detect the presence of those pathogenic bacteria that secrete them. By synthesizing lipids attached to dye moieties, it is possible to create substrates that will change color as they are hydrolyzed by secreted lipases. The dye molecule can be one of many commercially available molecules that are colorless when attached to fatty acids, and change color when the substrate is cleaved by lipase. An example of such a dye is Rhodamine-110 (available from Molecular probes, Eugene, Oreg.). This color change reaction forms the basis of a bacterial sensor, which can be incorporated into healthcare products including, but not limited to, wound dressings.

In another example, the method and/or biosensor of the present invention can be used to detect the presence or absence of autolytic enzymes. Autolysins are enzymes that degrade peptidoglycan, a component of the bacterial cell envelope. Autolytic enzymes serve to break down peptidoglycan, be it that of the parent organism, as part of cell division and turnover functions, or as a means to breakdown cell walls of competing bacteria. When labeled with para-nitrophenol, synthetic peptidoglycan subunits (such as, but not limited to, N-acetyl-β-d-glucosaminide) serve as indicators that can form the basis of a bacterial sensor.

In another example, the method and/or biosensor of the present invention can be used to detect the presence or absence of beta-galactosidase on the surface of bacteria cells. Most bacterial species express beta-galactosidase as a cytoplasmic enzyme involved in the metabolism of lactose as an energy source. Certain species of *Streptococcus*, however, display the enzyme on the surface of the cell. A labeled synthetic molecule that acts as a substrate for beta-galactosidase, (including, but not limited to ortho nitrophenyl β-D-galactopyranoside (ONPG)) could thus be used as a means of detecting streptococci in the environment.

A method for developing an assay for detecting a pathogenic bacteria that produces at least one enzyme that is secreted by the cell or present on the surface of the cell and a method for using the assay to detect pathogenic bacteria producing the enzyme(s) now follows:

Step 1) Define an amino acid sequence that uniquely identifies the prokaryotic microorganism of interest. Alternatively a (one or more) amino acid sequence that is unique to a specific group of pathogens, for example, wound-specific pathogens can be determined.

Select an amino acid sequence, for example, a protein, peptide, or polypeptide (marker sequence) that uniquely characterizes or marks the presence of the microorganism or group of microorganisms (for example, wound-specific pathogens) of interest. The selection can be performed utilizing a bioinfomatic approach, for example, as described in detail below. One or more amino acid sequences that are unique to a specific prokaryotic microorganism are determined.

Step 2) Obtain sufficient enzyme to determine conditions facilitating optimal modification of a substrate by the enzyme.

Isolate the enzyme from the extracellular medium in which the pathogenic bacteria to be assayed is growing, or from the cell membrane of the bacteria, using standard protein purification techniques, described, for example, in Ausubel (supra).

Alternatively, if the genetic sequence encoding the enzyme or the location of the genetic sequence encoding the enzyme are unknown, isolate and clone the genetic sequence encoding the marker amino acid of Step 1, or, first determine the genetic sequence, and then proceed as before.

Step 3) Determine the conditions for growth of the prokaryotic organism and for the production of an enzyme presented on the surface of the cell or secreted by the cell.

Determine medium required for growth of the specific prokaryotic microorganism of interest and for expression of its unique active enzyme into the medium. Also determine whether a second molecule, for example, an enzyme is required to convert the specific enzyme from an inactive precursor form to an active form. To determine if the enzyme has been secreted in an active form, a sample of the bacterial culture is provided with chosen potential substrates and cleavage of these substrates is determined. This can be done, for example, by combining the bacteria that produce the enzyme with the substrate in the appropriate media and incubating at 37° C. with gentle shaking. At preset times (0.1, 0.3, 1.0, 3.0, 5.0, 24 and 48 hours) the samples are centrifuged to spin down the bacteria, and a small aliquot is removed for an SDS-PAGE gel sample. After completion of the time course, the samples are run on a 10-15% gradient SDS-PAGE mini-gel. Then, the proteins are transferred to Immobilon Pseq (Transfer buffer, 10% CAPS, 10% methanol pH 11.0, 15 V for 30 minutes) using a Bio-Rad semi-dry transblotting apparatus. Following transfer of the proteins, the blot is stained with Coomassie blue R-250 (0.25% Coomassie Brilliant Blue R-250, 50% methanol, 10% acetic acid) and destained (high destain for 5 minutes, 50% methanol, 10% acetic acid; low destain until complete, 10% methanol, 10% acetic acid) followed by sequencing from the N-terminal. Alternatively, the samples can be run on a mass spectrometer in order to map the sites of proteolytic cleavage using, for example, a Voyager Elite Mass spectrometer (Perceptive Biosystems, Albertville, Minn.).

Step 4) Identify any specific substrate(s) of the active enzyme protease. Examples of potential substrates include proteins, peptides, polypeptides, lipids, and peptidoglycan subunits. Label each substrate with a detectable label, for example, a detectable label described herein, or any other detectable label known in the art.

Step 5) Increase the specificity of the enzyme-substrate interaction (optional) by determining the active or binding site of the enzyme (for example, using FRET as described above), then determining the genetic sequence useful for producing the active or binding site, and cloning the determined genetic sequence to generate a more specific substrate.

Step 6) Provide a biosensor comprising one or more of the detectably labeled substrates identified above for detection of the protease of the pathogenic bacteria of interest.

The substrate can be attached to solid support, for example, a wound dressing, or an article that holds the enzyme and substrate, for example, a body fluid collection tube or bag, a microplate well, or a test tube. The solid support, if desired, can provide a plurality of derivatized binding sites for coupling to the substrate, for example, succimidyl ester labeled primary amine sites on derivatized plates (Xenobind plates, Xenopore Corp., Hawthorne, N.J.).

Optionally, unoccupied reactive sites on the solid support are blocked by coupling bovine serum albumin, or the active domain of p26 thereto. p26 is an alpha-crystallin type protein that is used in this case to reduce non-specific protein aggregation. The ability of the p26 protein to refold heat denatured citrate synthetase before and after coupling to the surface of the food packaging is used as a control for determining p26 activity. Alpha-crystallin type proteins were recombinantly produced using standard recombinant DNA technologies (see Ausubel, supra). Briefly, the plasmid containing the beta sheet-charged core domain of p26 is electroporated into electrocompetent BL21(DE3) cells (Bio-Rad *E. coli* pulser). The cells are grown up to an $OD_{600}$ of 0.8, then induced with 1 mM IPTG for 4 hours. The cells are spun down, and sonicated in low buffer (10 mM Tris, pH 8.0, 500 mM NaCl, 50 mM Imidizole) to lyse (Virsonic, Virtis, Gardiner, N.Y.). The lysate is spun down at 13,000×g for 10 minutes, and the supernatant 0.45 and 0.2 µm filtered. This filtrate is loaded onto a Ni-NTA superose column (Qiagen, Valencia, Calif., cat # 30410). High buffer (10 mM Tris pH 8.0, 500 mM NaCl, 250 mM Imidizole) is used to elute the protein.

Allow the enzyme(s) to come into contact with the substrate(s), and monitor the reaction for a modification in the detectably labeled substrate, as described herein. Modification of the substrate indicates that the enzyme produced/secreted by the bacteria is present in the reaction. In addition, the absence of modification of the substrate indicates that the enzyme is not present in the sample. If the bacteria or enzyme is from a wound, modification of the substrate indicates that the bacteria is present in the wound, and that the wound is infected, while the absence of modification of the substrate indicates that the particular bacteria is not present in the wound, and that the wound is not infected with that particular bacteria.

EXAMPLES

The present invention will now be illustrated by the following Examples, which are not intended to be limiting in any way.

Example 1

Identification of Wound-Specific Proteins

The TIGR comprehensive microbial resource multi genomic analysis tools located at the following Internet site: http://www.tigr.org/tigr-scripts/CMR2/select_genomes.spl?showref=true&reforg=0&cutoff=60&logic=AND&showheader=true, as available on Jun. 18, 2001 were used to analyze the complete genome sequences of the following common wound pathogen species: *Staphylococcus aureus* (*S. aureus*), *Staphylococcus epidermidis, Streptococcus pyogenes, Pseudomonas aeruginosa, Enterococcus faecalis,* and *Escherichia coli*. Specifically, each gene in the *S. aureus* genome was compared for homologs in each of the other above specified genomes. Any *S. aureus* gene that did not have a homolog (with at least 45% identity at the amino acid level) to all 5 pathogens, was discarded. The remaining pool contained only those genes that are common to these six major wound pathogens. These searches were conducted using the default settings as parameters.

To identify wound-specific genes, the genomes of 47 other non-wound-pathogenic bacteria were then used to identify those genes that are common to the wound pathogens, but not to the other 47 non-wound infecting bacteria. This screening resulted in the examination of 132,313 genes that were compared to the wound pathogen genomes. After subtracting those genes with greater than 45% homology to non-wound pathogens, using the same comparison parameters as above, 131 genes of known function were identified as wound-specific. Subsequent analysis of the 131 genes revealed that they fell roughly into the following nine groups based upon their predicted function:

1) Lysins; enzymes that function to lyse host cells or competing bacterial cells.
2) Putative exotoxins; proteins that are homologous to certain secreted toxins of the staphylococci. These proteins have enzyme signatures from block searches of exotoxins including topoisomerase I, synapsin-like, and aminopeptidase.
3) Cell wall machinery; enzymes involved in the synthesis and turnover of bacterial cell wall components, including peptidoglycan.
4) Matrix binding proteins; proteins that allow bacteria to bind to the extracellular matrix molecules of the host environment (fibronectin and fibrinogen). These proteins have enzyme signatures from block searches including specific recombinase, adenylate cyclases class-I, and NADH-ubiquinone oxidoreductase.
5) Proteases; enzymes that either specifically or non-specifically digest other protein molecules.
6) Hydrolases; enzymes that break down polymeric molecules into their subunits.
7) Metabolic proteins; a broad class of enzymes designed to perform various housekeeping functions of the cell, such as breaking down nutrients into components that are useful to the cell.
8) Transcription factors; proteins involved in the control of DNA transcription.
9) Virulence factors; general class of proteins that are required by the bacterial cell to cause an infection. These proteins have enzyme signatures from block searches of virulence factors, including glycoside hydrolases.

The following wound-specific enzymes were identified according to the sequence comparison methods described above (the GenBank Accession Number and/or protein name for an example of each protein is provided in parentheses): autolysin (Atl), FemB protein (femB), fmhA protein (fmhA), TcaB protein (tcaB), enterotoxin P (sep), exotoxin 6 (set6), exotoxin 7 (set7), exotoxin 8 (set8), exotoxin 9 (set9), exotoxin 10 (set10), exotoxin 11 (set11), exotoxin 12 (set12), exotoxin 13 (set13), exotoxin 14 (set14), exotoxin 15 (set15), Clumping factor B (clfB), Blt-like protein (SA1269), FmhC protein (fmhC(eprh)), enterotoxin SEM (sem), enterotoxin SeN (sen), enterotoxin SeO (seo), leukotoxin LukE (lukE), truncated integrase (SA0356), enterotoxin typeC3 (sec3), enterotoxin Yent1 (yent1), enterotoxin YENT2 (yent2), glycerol ester hydrolase (geh), immunodominant antigen A (isaA), serine protease SplB (splB), serine protease SplC (splC), ABC transporter permease (vraG), phosphomevalonate kinase (mvaK2), gamma-hemolysin component B (hlgB), gamma-hemolysin component C (hlgC), tagatose-6-phosphate kinase (lacC), cysteine protease precursor (sspB), 6-phospho-beta-galactosidase (lacG), extracellular enterotoxin L (sel), triacylglycerol lipase precursor (lip), Staphopain, Cysteine Proteinase (SA1725), tagatose 1,6-diphosphate aldolase (lacD), gamma-hemolysin chain II precursor (hlgA), enterotoxin homolog (SA1429), mannitol-1-phosphate 5-dehydrogenase (mtlD), staphylococcal accessory regulator A (sarA), lactose phosphotransferase system repressor (lacR), capsular polysaccharide biosynthesis (SA2457), capA, galactose-6-phosphate isomerase LacA subunit (lacA), fibrinogen-binding protein A, clumping factor (clfA), extracellular enterotoxin type G precursor (seg), extracellular enterotoxin type I precursor (sei), leukotoxin, LukD [Pathogenicity island SaPIn3] (lukD), fibronectin-binding protein homolog (fnb), fibronectin-binding protein homolog (fnbB), holin homolog [Bacteriophage phiN315] (SA1760), similar to D-xylulose reductase (SA2191), secretory antigen precursor SsaA homolog (ssaA), factor essential for expression of methicillin resistance (femA), similar to exotoxin 2 (SA0357), similar to exotoxin 1 (SA1009), similar to exotoxin 4 (SA1010), similar to exotoxin 3 (SA1011), staphylococcal accessory regulator A homolog (sarH3), similar to transaldolase (SA1599), similar to 5-nucleotidase (SA0022), undecaprenyl-PP-MurNAc-pentapeptide-UDPGlcNAc GlcNAc transferase (murG), similar to exonuclease SbcD (SA1180), similar to membrane protein (SA2148), Ser-Asp rich fibrinogen-binding, bone sialoprotein-binding protein (sdrC), Ser-Asp rich fibrinogen-binding, bone sialoprotein-binding protein (sdrD), Ser-Asp rich fibrinogen-binding, bone sialoprotein-binding protein (sdrE), similar to oligoendopeptidase (SA1216), similar to MHC class II analog (SA2006), similar to transcription factor (SA0858), probable beta-lactamase [Pathogenicity island SaPIn3] (SA1633), similar to NA(+)/H(+) exchanger (SA2228), similar to xylitol dehydrogenase (SA0242), similar to cell wall enzyme EbsB (SA1266), similar to transposase for IS232 (SAS069), similar to transposase for IS232 (SAS070), similar to transport protein SgaT (SA0318), similar to transcription regulator (SA0187), similar to ribose transporter RbsU (SA0260), similar to regulatory protein PfoR (SA0298), similar to enterotoxin A precursor (SA1430), similar to regulatory protein pfoR (SA2320), transposase homolog for IS232 [Pathogenicity island SaPIn3] (tnp), similar to formate transporter NirC (SA0293), similar to D-octopine dehydrogenase (SA2095), similar to rbs operon repressor RbsR (SA0261), similar to cell surface protein Map-w (SA0841), similar to fibrinogen-binding protein (SA1000), similar to fibrinogen-binding protein (SA1003), similar to fibrinogen-binding protein (SA1004), similar to staphylocoagulase precursor (SA0743), similar to ferrichrome ABC transporter (SA0980), similar to peptide binding protein OppA (SA0849), similar to proton antiporter efflux pump (SA0263), similar to kdp operon sensor protein (kdpD(SCCmec)), similar to secretory antigen precursor SsaA(SA0270), similar to outer membrane protein precursor (SA0295), similar to deoxyribodipyrimidine photolyase (SA0646), similar to secretory antigen precursor SsaA (SA2097), similar to integral membrane efflux protein (SA2233), similar to secretory antigen precursor SsaA (SA2332), similar to secretory antigen precursor SsaA (SA2353), similar to transmembrane efflux pump protein (SA0099), similar to multi-drug resistance efflux pump (SA0115), probable specificity determinant HsdS [Pathogenicity island SaPIn3] (SA1625), similar to ABC transporter ATP-binding protein (SA0339), similar to cobalamin synthesis related protein (SA0642), similar to transcription regulator MarR family (SA2060), similar to N-Carbamoylsarcosine Amidohydrolase (SA2438), similar to teichoic acid biosynthesis protein B (SA0243), similar to teichoic acid biosynthesis protein B (SA0247), similar to transcription regulator, RpiR family (SA2108), similar to two component sensor histidine kinase (SA2180), similar to succinyl-diaminopimelate desuccinylase (SA1814), similar to extracellular matrix and plasma binding (SA0745), similar to transcription antiterminator BglG family (SA1961), similar to cobalamin synthesis related protein CobW (SA2368), similar to DNA polymerase III, alpha chain PolC type (SA1710), similar to spermine/spermidine acetyltransferase blt (SA1931), similar to trimethylamine dehydrogenase (EC 1.5.99.7) (SA0311), similar to AraC/XylS family transcriptional regulator (SA0622), similar to PTS fructose-specific enzyme IIBC component (SA0320), similar to beta-lactamase [Pathogenicity island SaPIn1] (SA1818), similar to 4-diphosphocytidyl-2C-methyl-D-erythritol synthase (SA0241), similar to synergohymenotropic toxin precursor—*Staphylococcus intermedius* (SA1812), similar to bacteriophage terminase small subunit [Pathogenicity island SaPIn1] (SA1820), similar to poly (glycerol-phosphate) alpha-glucosyltransferase (teichoic acid biosynthesis)(SA0523). Some of the above identified enzymes are proteins that have known enzymatic activity, while other proteins have enzyme signatures obtained from block searches. Therefore, it is reasonable to believe that proteins containing enzymes signatures are suitable for use as enzymes.

Example 2

Preparation of Bacteria for Detection of the Absence or Presence of Bacteria in a Sample A culture of each of the following bacterial species was grown to saturation in Brain Heart Infusion (BHI) broth at 37° C. with vigorous shaking (~200 rpm), using methods that are standard in the art: *Staphylococcus aureus; Staphylococcus epidermidis; Serratia marcescens; Streptococcus salivarius; Escherichia coli; Pseudomonas aeruginosa*; and *Enterococcus faecalis*. After overnight growth (to saturation), a 1 mL sample of each culture was obtained, and the cells were removed from the culture supernatant by centrifugation at 12,000×g for 5 minutes. The remaining culture supernatants were stored on ice until required (less than one hour). The bacteria were assayed for the presence or absence of specific enzymes as described below. Alternatively, the bacterial cells are not separated from the culture supernatant, but rather, the assay is carried out on a sample containing the cells still in suspension in their culture broth.

Example 3

Detection of *Serratia marcescens* Using a Protease Assay

A protease is an enzyme that is responsible for the degradation of proteins by hydrolysis of peptide bonds. A protease can be either general or specific in its target sequence, depending on its purpose. Pathogenic bacteria secrete some proteases that are specific in nature and target a select protein or peptide for the purpose of either attack of other cells or as a defense mechanism. The target of a specific protease is identified by the amino acid sequence of the protein adjacent to the cleavage site.

A *Serratia marcescens* specific protease was identified based on a homology search using the sequence of a known sspB protease found in the *Staphylococcus* species. This protease has homology to the cysteine protease precursor (sspB) protein of *Staphylococcus aureus*. The corresponding *Serratia* protease has not been previously characterized. To test for the presence of the specific protease in a bacterial culture, a short target peptide was designed. This target peptide was derived from a polypeptide substrate previously shown to be cleaved by *S. aureus* sspB (Chan and Foster, J. Bacteriology 180:6232-6241, 1998). This peptide was capped by a fluorescent dye molecule on one end and by an associated chromophore molecule on the other end. If the absorption band of the chromophore has sufficient overlap with the absorbance band associated with the fluorescence of the dye molecule, the observed fluorescence will be quenched. This phenomenon is known as fluorescence resonance energy transfer (FRET) and can be used to determine the distance between the FRET donor and acceptor molecules. Upon cleavage of the peptide the fluorescent indicator is released from the proximity of the quencher and the fluorescence increase is measured. Thus, the presence or absence of a protease that targets the peptide in the sample can be determined by detecting fluorescence emitted by the cleaved peptide.

The specificity of the protease for *Serratia marcescens* is was determined by detecting cleavage of a target polypeptide, using FRET, by the protease in a number of different bacterial pathogen samples. The bacterial pathogen samples used in this study were all taken from overnight cultures grown in brain heart infarction (BHI) media at 37° C., as described herein. The bacterial pathogens chosen for this study were: *Staphylococcus aureus, Listeria monocytogenes, Pseudomonas aeruginosa, Enterococcus faecalis, Streptococcus salivarius, Serratia marcescens*, and *Escherichia coli*. The target peptide substrate used to test for the *Serratia marcescens* specific protease was as follows: Dabsyl-NEAIQEDQVQYE-Edans (SEQ ID NO: 2), and was prepared using standard methods known to one skilled in the art. A substrate solution containing 1 mg/mL to 5 mg/mL of target peptide substrate in 1:1 water/dimethylsulfoxide (DMSO) was prepared. The reaction buffer used was 20 mM Tris (pH 7.5) with 200 mM NaCl. The assay was carried out using 3 µL of substrate solution, 7 µL of bacterial culture medium, and 140 µL of reaction buffer, for a total volume of 150 µL of assay mixture. The assay mixture was loaded into individual wells of a microtiter plate and the plate was placed in a fluorimeter. The narrow band filters in the fluorimeter were centered at 305 nm for excitation and 485 nm for fluorescence emission readings. The samples were incubated at 37° C. and the fluorescence of each sample was measured at time points taken every 10 minutes. A sample containing substrate, reaction buffer, and water in place of the bacterial control was used as a negative control.

The results of this study are shown in FIG. 1, which is a graph showing the change in relative fluorescence intensity over time for samples containing an active bacterial culture (grown overnight in BHI media) or a water control, substrate, and reaction buffer. Culture medium containing *S. marcescens* cells reacted with the substrate, giving rise to an increase in fluorescence intensity over the course of the reaction. None of the other bacterial samples, including the *Staphylococcus aureus* sample, were distinguishable from the control reaction containing water. Furthermore, the reaction took only minutes to distinguish the sample containing *S. marcescens* from the others tested here. Thus, this assay can be used as a specific detection system for the presence of *S. marcescens* in a sample.

Example 4

The *Serratia* Specific Protease is Exported from the Cell

Another experiment was performed to determine whether the *Serratia* specific protease is found on the cell surface or if the cell exports the protein into the media. If the protease is exported, it may then be able to diffuse through the media towards its substrate. If not, then the bacteria would have to be in contact with the substrate to allow detection of the presence of the pathogen in the sample. Such an assay was carried out as described below.

An *S. marcescens* culture was grown overnight in BHI. The cells were separated from the culture media by centrifugation so that the activity associated with each could be measured. The cell pellets were washed and then re-dissolved in buffer to give the original volume. The proteolytic activity of the washed cells was then compared to the proteolytic activity of the supernatant media in the *Serratia* protease assay, described above. Seven µL aliquots of each sample were run using the assay conditions described above (using 3 µL of substrate solution and 140 µL of 20 mM Tris buffer (pH 7.5) with 200 mM NaCl added).

Figure 2:
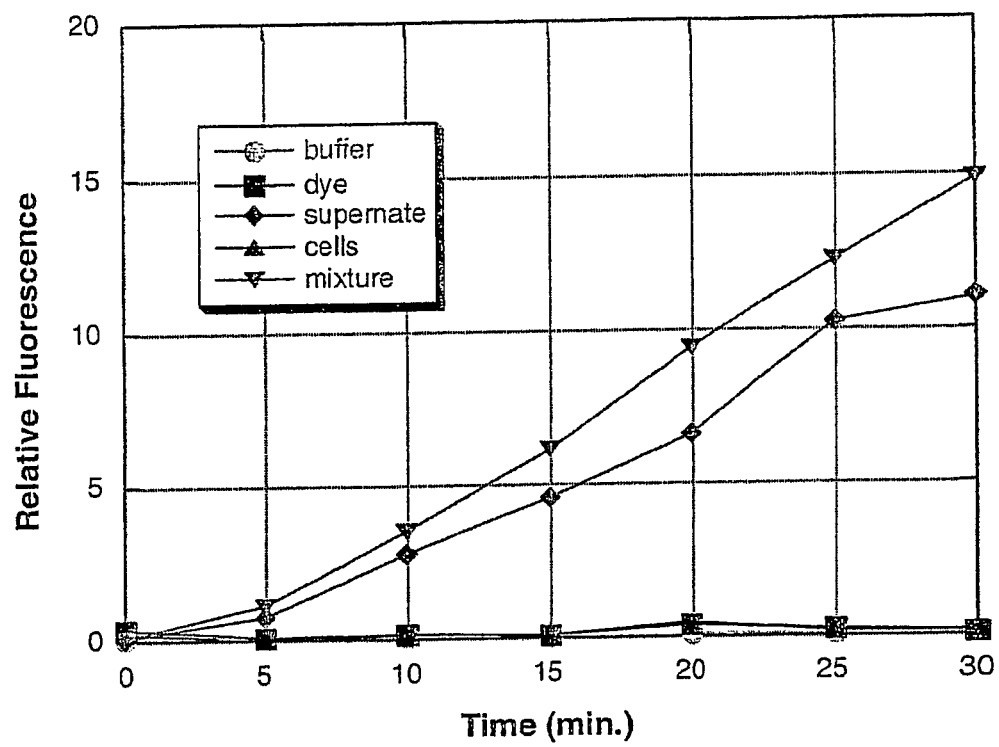
FIG. 2 is a graph of the cleavage of a target polypeptide substrate (relative fluorescence) over time (minutes) in samples containing buffer, substrate solution only (dye), supernatant (containing no cells), S. marcescens cells, or S. marcescens bacterial culture (mixture).

The results obtained for this experiment are shown in FIG. 2, which is a graph of the relative fluorescence of the target peptide, indicating the amount of peptide cleavage in samples containing buffer, substrate solution only (dye), supernate (containing no cells), *S. marcescens* cells, or *S. marcescens* bacterial culture (mixture) over time. The sample labeled "mixture" contains the original overnight growth media containing active *Serratia* cultures that was used to generate the samples of cells and supernatant. As shown in FIG. 2, the protease activity obtained from the supernatant sample was nearly equivalent to the protease activity for the overnight culture. The sample obtained from the cell pellet did not show any activity and was in the same range as the buffer and dye controls. These results show that the *Serratia* protease is exported from the cell and can diffuse away from the cell surface into the media. These results thus indicate that a *Serratia* cell in a sample does not have to come into direct contact with its target substrate in order to be detected.

Example 5

Activity of the *Serratia* Specific Protease Under Various Growth Conditions

The stage of enzyme production and/or export from a pathogen is also a factor to be taken into consideration when designing methods and biosensors for detecting wound specific-pathogens in a sample. The synthesis and export of a bacterial protease can be regulated by the growth conditions. Some proteases produced by pathogenic bacteria are induced under growth limiting conditions. To investigate the growth conditions by which the *S. marcescens* specific protease was expressed, the activity of the protease (cleavage of the target polypeptide) produced by cells that were grown overnight to stationary phase was compared to the activity of the protease produced by cells that had been actively growing in log phase conditions for several hours.

Figure 3:
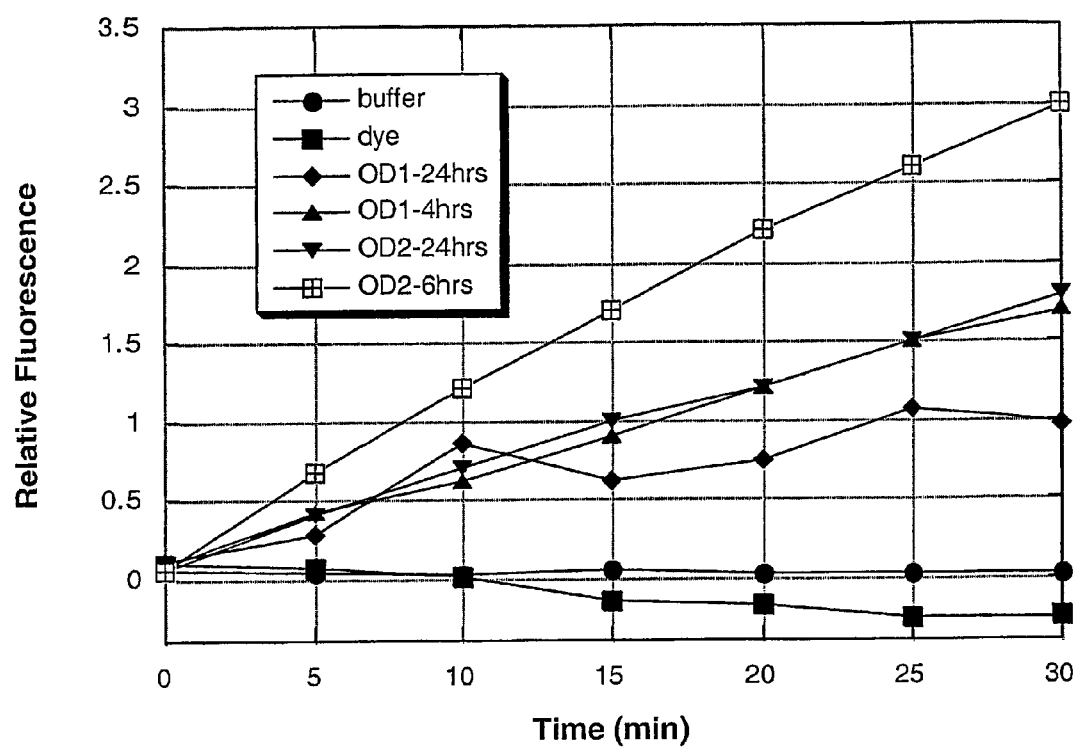
FIG. 3 is a graph of the cleavage of a target polypeptide substrate (relative fluorescence) over time (minutes) in S. marcescens cultures grown for 4 hours and diluted to an OD of 1 (log phase); S. marcescens cultures grown for 24 hours and diluted to an OD of 1 (stationary phase); S. marcescens cultures grown for 6 hours and diluted to an OD of 2 (log phase); S. marcescens cultures grown for 24 hours and diluted to an OD of 2 (stationary phase), or control samples containing either buffer or dye.

The optical density (OD) of the samples used in this experiment was adjusted by dilution in order to account for cell density differences during growth. The overnight cultures were diluted with BHI media to give samples with an OD of 1 or 2 for comparative activity measurements. *S. marcescens* specific protease activity was assessed as described herein, by measuring the relative fluorescence of the cleaved target polypeptide. The volume of the bacterial cell cultures, the substrate solution (dye), and the reaction buffer added remained constant. The assay conditions used for this experiment were the same as described above. The results of these studies are shown in FIG. 3, which is a graph of the relative fluorescence of cleaved target polypeptide by *S. marcescens* cultures grown for 4 hours and diluted to an OD of 1 (log phase); *S. marcescens* cultures grown for 24 hours and diluted to an OD of 1 (stationary phase); *S. marcescens* cultures grown for 6 hours and diluted to an OD of 2 (log phase); *S. marcescens* cultures grown for 24 hours and diluted to an OD of 2 (stationary phase), or control samples containing either buffer or dye. As shown in FIG. 3, the activity observed for the log phase samples were both higher than the corresponding stationary phase samples of the same OD, however the protease was present and readily detectable in both the log and stationary phases of cell growth. These results demonstrate the ability of the *S. marcescens* protease assay to be both rapid and specific. In addition, the assay was shown to be robust under various pathogen growth conditions.

Example 6

Activity of the *Serratia* Specific Protease Under Various pH Conditions

The conditions for which a pathogen detection assay is suitable was studied in order to determine the range of applicability of the assay. Some of the relevant parameters include pH, temperature, salt concentration, and nutrient availability. Physiological data is known for some of these parameters, however the conditions in a wound may vary in such things as pH and nutrient availability. To address these issues, further experiments were performed to determine the pH range for the *Serratia* protease activity.

Figure 4:
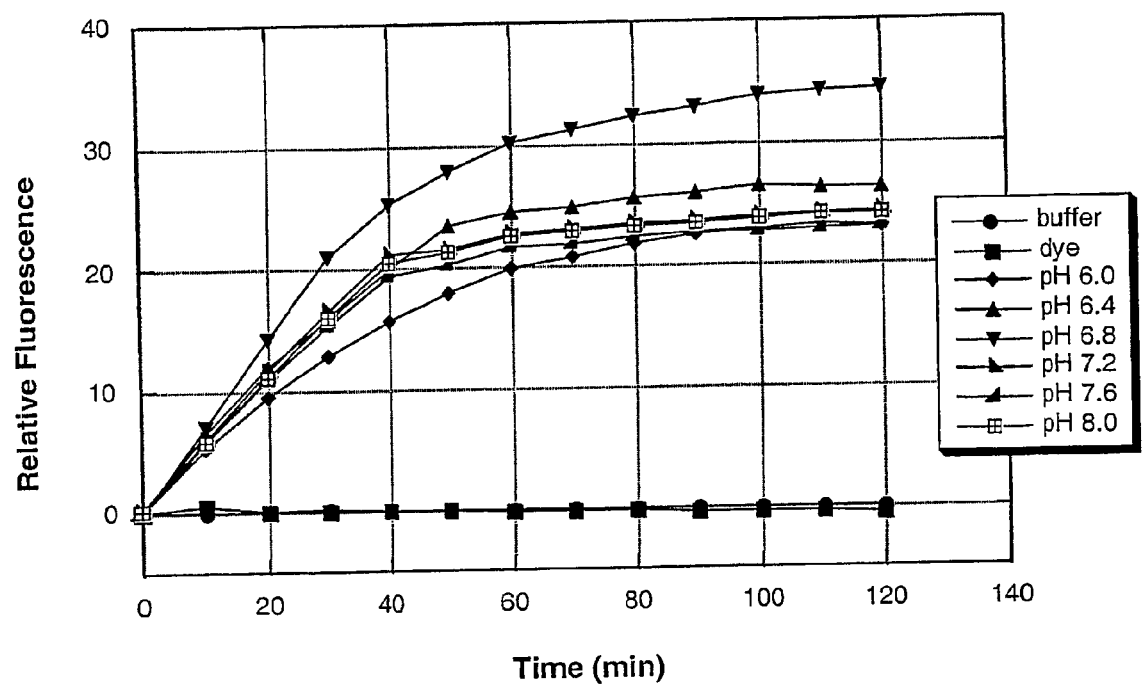
FIG. 4 is a graph of the cleavage of a target polypeptide substrate (relative fluorescence) in S. marcescens cultures having a pH level of 6, 6.4, 6.8, 7.2, 7.6, or 8.0 over time (minutes).

The pH dependence experiment was carried out using the supernatant obtained by centrifugation of an overnight culture of *S. marcescens* and the FRET assay described herein. The assay solution was buffered with 20 mM sodium phosphate at 6 different pH levels: pH 6, 6.4, 6.8, 7.2, 7.6, and 8.0. The salt concentration used was constant at 200 mM NaCl. The volumes of both the supernatant and the substrate solution (dye) remained the same as those used in the studies described above. The results of this study are shown in FIG. 4, which is a graph of the relative fluorescence of the samples having different pH levels over time. The optimum pH for *Serratia* protease is 6.8, however the activity does not vary much over the pH range studied here. The useful range of this assay extends from below pH 6 to above pH 8. This indicates that the *Serratia* protease is robust under a wide range of pH conditions, and therefore appears to be a good assay target for a wound infection sensor.

Example 7

The *Serratia* Specific Protease is not a Metalloprotease

Several types of proteases are found in bacteria and are categorized by the catalytic group used in the active site. The most common bacterial proteases are the serine protease, the cysteine protease, and the metalloprotease. The metalloprotease is so named because it contains a catalytic zinc ion at the active site. The bound zinc ion is generally labile and can be removed by chelation. Therefore, reduction of the activity by addition of a chelator to the assay buffer indicates the protease is most likely a metalloprotease.

Figure 5:
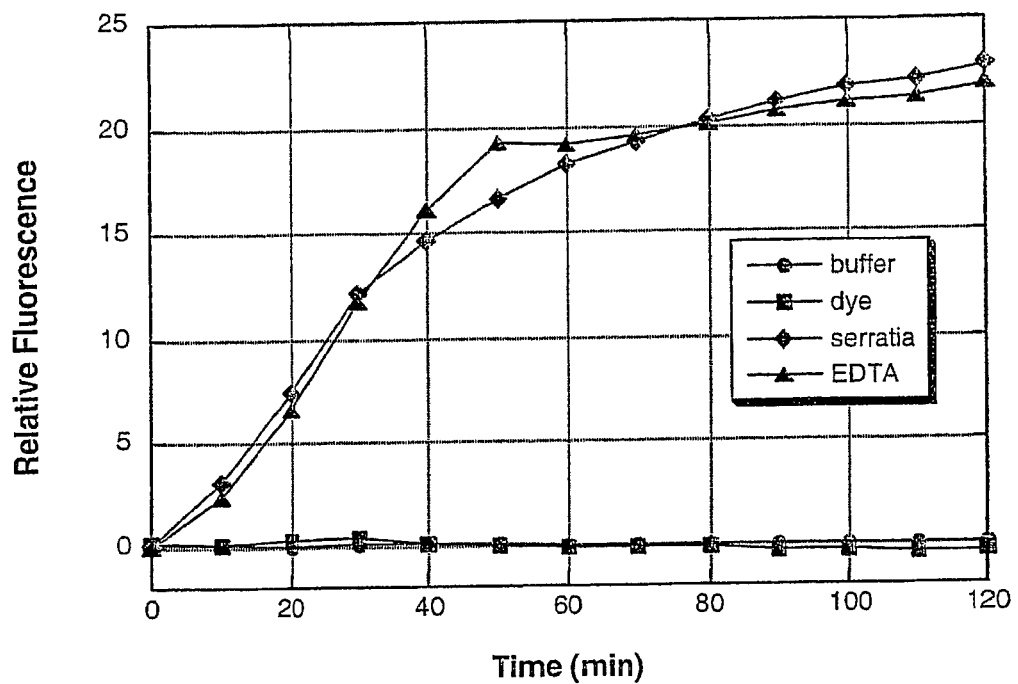
FIG. 5 is a graph of the cleavage of a target polypeptide substrate (relative fluorescence) in samples containing Serratia culture, Serratia culture plus EDTA, or buffer or substrate solution (dye) only (controls) over time (minutes).

To determine whether the *Serratia* specific protease is a metalloprotease, the following study was performed. One mM ethylenediaminetetraacetic acid (EDTA) was added to the standard assay solution (20 mM Tris (pH 7.5) with 200 mM NaCl) used in the above-described FRET assay, and its effect on protease activity (measured as a decrease in relative fluorescence activity of the protease) was determined. FIG. 5 is a graph of the effect of EDTA on the protease activity, measured by relative fluorescence of the target peptide in samples containing *Serratia* culture, *Serratia* culture plus EDTA, or buffer or substrate solution (dye) only (controls). No reduction in activity was found for the sample containing EDTA when compared to native activity, indicating that the *Serratia* protease is probably a serine protease or a cysteine protease.

Example 8

A Biosensor for Detection of *Serratia marcescens*

Figures 6A, 6B, 6C:
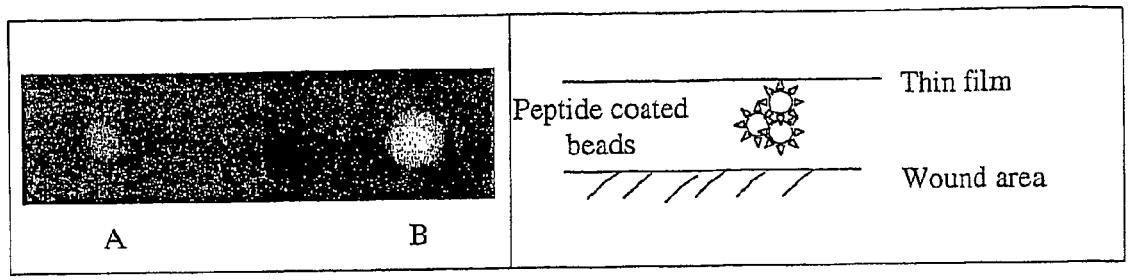
FIG. 6A is a scanned image of the fluorescence of a biosensor containing Cell Debris Remover in which the Serratia marcescens specific protease target peptide was not bound to it, in the presence of Serratia extracts.
FIG. 6B is a scanned image of the fluorescence intensity of a biosensor containing Cell Debris Remover in which the Serratia marcescens specific protease target polypeptide was bound to it, in the presence of Serratia extracts.
FIG. 6C is a schematic representation of a biosensor for detection of a Serratia marcescens specific protease.

An example of a biosensor for the detection of a *Serratia marcescens* (*S. marcescens*) specific protease, and therefore, for the detection of *Serratia marcescens* now follows. The *Serratia marcescens* specific target peptide substrate was bound to a surface with a weak positive charge, such as fibrous cellulose lightly substituted with DEAE (Cell Debris Remover, Whatman, Inc.). This matrix was placed under a film, for example, a clear bandage, as shown in FIG. 6C, and fluorescence in the presence of *Serratia* was detected. The efficacy of this biosensor was demonstrated by exposing the biosensor containing Cell Debris Remover in which the *Serratia marcescens* specific protease target peptide was not bound to it (FIG. 6A; negative control biosensor), or a biosensor containing Cell Debris Remover in which the *Serratia marcescens* specific protease did contain the target polypeptide (FIG. 6B) to *Serratia marcescens* extract. Very little fluorescence was emitted from the control biosensor, while fluorescence was readily detected in the biosensor containing the target peptide. These results demonstrate that such a solid phase wound infection biosensor consisting of the peptide bound to Cell Debris Remover can be used to detect the *Serratia* pathogen in a wound or any other sample or surface containing the pathogen.

The above studies demonstrate the identification of a novel peptide substrate that is specific for *S. marcescens*. The activity associated with this protease appears to be novel. The studies described herein also indicate that the *S. marcescens* specific protease is secreted and the protease is present in all phases of growth. In addition, the detection assay is robust under various pH conditions, demonstrating that this *S. marcescens* specific protease can be used for the for detection of *S. marcescens* in a sample.

Example 9

Detection of the Presence of *Staphylococcus aureus* and *Staphylococcus epidermidis* Using a Lipase Assay Certain bacteria secrete lipases into their environment as part of their survival and/or virulence mechanisms. The lipases serve to break down lipids in the growth environment in order to release nutrients. Lipases may also play a role in disarming mammalian host defenses during infection. Lipases fall into the category of secreted hydrolases from the list outlined above.

To test for the presence or absence of lipases secreted by bacteria, the lipase substrate p-nitrophenyl caprate, obtained from Sigma (Catalog No.: N-0252). This lipase substrate consists of capric acid, a ten-carbon lipid molecule, esterified with the dye para nitrophenol (detectable label) as described above. The substrate was dissolved in isopropyl alcohol at a concentration of 8 mM (2.35 mg/mL). A reaction buffer containing 20 mM Tris (pH 8.5) was also prepared.

To perform the lipase assay, 80 μL of reaction buffer, 10 μL of culture supernatant from each bacteria species described in Example 2, and 10 μL of assay substrate were added to a well of a 96-well microplate. Each bacterial species was assayed individually, and the assays were performed in triplicate. The 96-well plate was incubated at 37° C. for 60 minutes. At 5 minute intervals during the incubation period, absorbance at 415 nm, indicating modification of the enzyme by a lipase secreted by the cells, was automatically measured using a BioRad Benchmark Microplate reader.

Figure 7A:
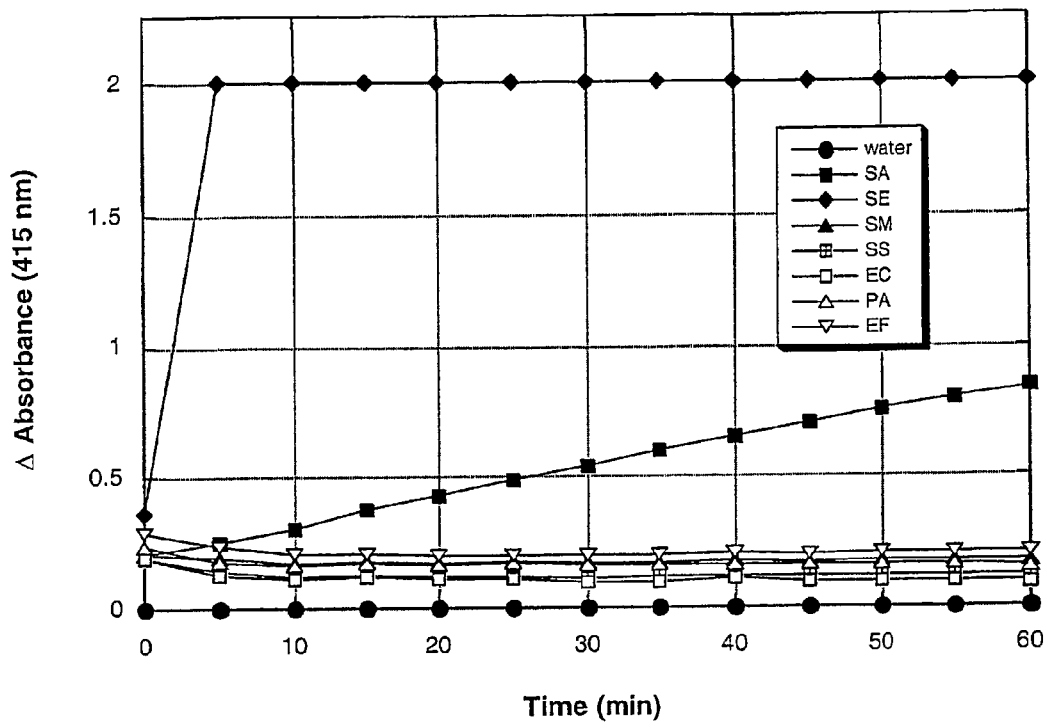
FIG. 7A is a graph of the cleavage (absorbance) of target substrate in samples containing bacterial supernatant, assay substrate (p-nitrophenyl caprate), and reaction buffer at 415 nm over time (minutes). (SA=Staphylococcus aureus; SE=Staphylococcus epidermidis; SM=Serratia marcescens; SS=Streptococcus salivarius; EC=Escherichia coli; PA=Pseudomonas aeruginosa; EF=Enterococcus faecalis)

FIG. 7A is a graph showing the results of the lipase assay, measured as the absorbance at 415 nm over a period of 60 minutes. As shown in FIG. 7A, labeled substrate incubated with culture supernatants from *Staphylococcus epidermidis* (*S. epidermidis*) and *Staphylococcus aureus* (*S. aureus*) showed a dramatic color change, as detected by absorbance at 415 nm after just a few minutes. Other bacterial samples showed no color change, although a slight increase in turbidity contributed to the absorbance at 415 nm. This lipase assay is therefore suitable for the detection of *Staphylococcus aureus* or *Staphylococcus epidermidis* in a sample. Modification of p-nitrophenyl caprate by a bacterial sample indicates that the bacteria can be *Staphylococcus*. In addition, the absence of modification of p-nitrophenyl caprate by a bacterial sample can indicate that the bacteria is not *Staphylococcus*.

Figure 7B:
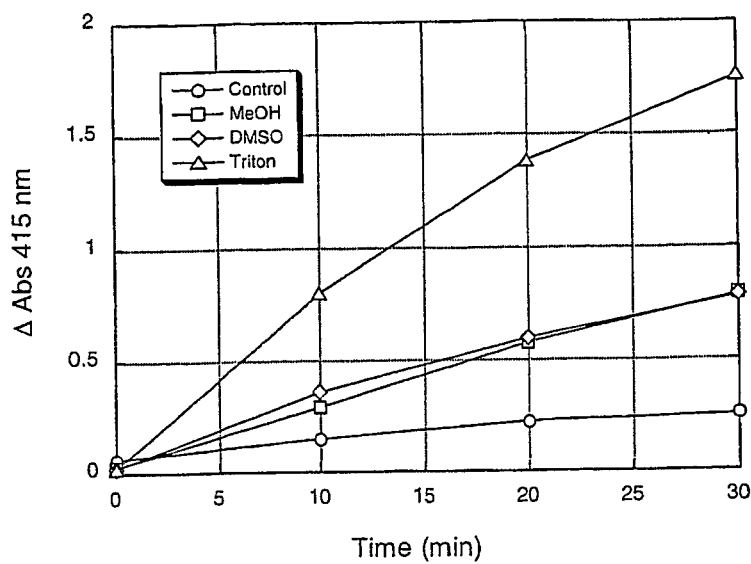
FIG. 7B is a graph of the cleavage of target substrate (Δ Abs) in samples containing S. aureus bacterial supernatant, assay substrate (p-nitrophenyl caprate), and reaction buffer at 415 nm over time (minutes). The reaction buffer consisted of 20 mM Tris (pH 8.3) with 1 mM $ZnSO_4$ added, plus either nothing additional (control), 20% methanol (MeOH), 20% DMSO (DMSO), or 10 mM Triton X-100 (Triton).

Other major wound pathogens also secrete lipolytic enzymes into their growth medium (Rosenau and Jaeger, Biochime, 82: 1023, 2000), so it may seem surprising that other organisms do not react with this substrate. However, it is known that bacterial lipases do show strong substrate specificity with regard to the chain length of the fatty acid they hydrolyze (Van Kampen et al., BBA, 1544: 229, 2001) and to the location in a lipid layer. The degree that the environment of the substrate affects the efficiency of hydrolysis depends on the particular enzyme. To test this for the lipase from *S. aureus*, the above-described lipase assay was performed in the presence of several detergent and solvent additives. The reaction buffer consisted of 20 mM Tris (pH 8.3) with 1 mM $ZnSO_4$ added, plus either nothing additional (control), 20% methanol, 20% DMSO, or 10 mM Triton X-100. As shown in FIG. 7B, the hydrolysis rate was found to increase in the presence of organic solvents such as methanol and DMSO, and in the presence of the detergent Triton X-100.

Example 10

Detection of the Presence of *Enterococcus faecalis* Using an Autolysin Assay

Autolysins are enzymes that degrade peptidoglycan, a component of the bacterial cell envelope. Autolytic enzymes serve to break down peptidoglycan, be it that of the parent organism, as part of cell division and turnover functions, or as a means to breakdown cell walls of competing bacteria. Autolysins fall into the category of "cell wall machinery" in the list of categories detailed above.

To test for the presence of autolysins in bacterial cell culture supernatants, the synthetic autolysin substrate p-nitrophenyl-N-acetyl-b-D-glucosaminide (PNP-AGA), a substrate containing a dye that is detected at 415 nm when the substrate is modified, was dissolved in 50% DMSO to a final concentration of 20 mM to form a substrate solution. Modification of this substrate can be detected by measuring the change in absorbance at 405 nm. A reaction buffer containing 20 mM $NaPO_4$ and 200 mM NaCl (pH 7.0) was also prepared. The assay was performed as follows. Five-hundred µL of reaction buffer, 50 µL of substrate solution (20 mM PNP-AGA), and 450 µL of test sample (bacterial supernatant as described in Example 2, or water (control)) were added to a reaction tube. Each bacterial species was assayed individually. The samples were incubated at 20° C. for 7 hours. The progress of modification of the labeled substrate was monitored by absorbance at 405 nm.

Figure 8:
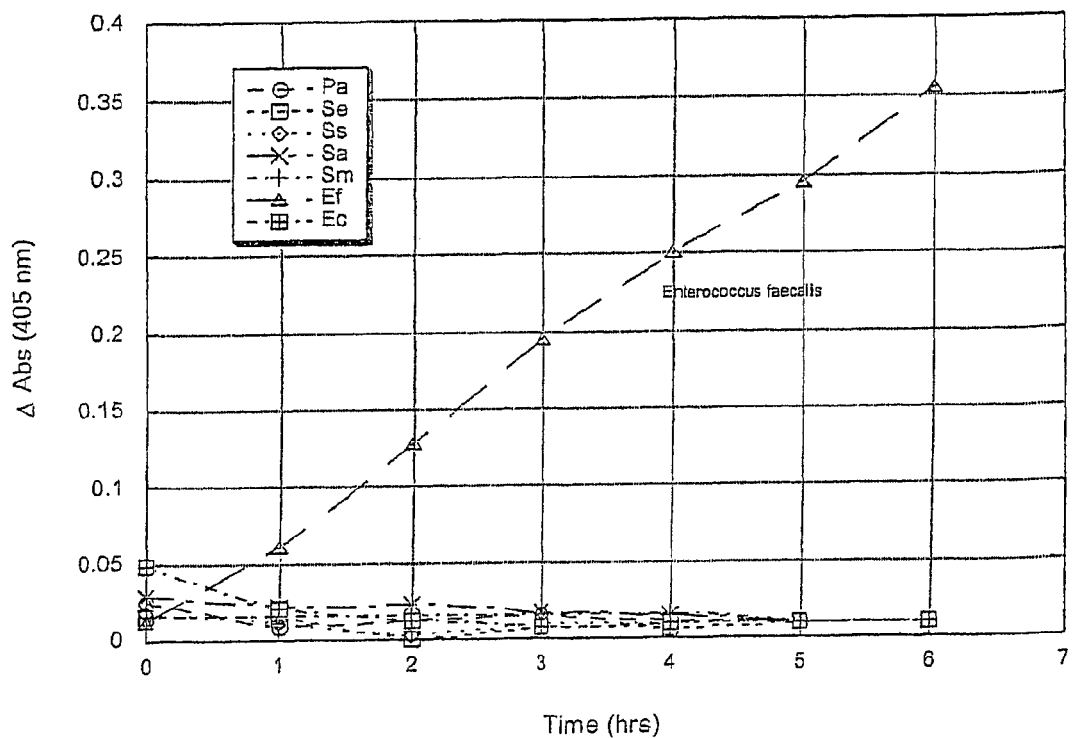
FIG. 8 is a graph of the change in absorbance (Δ Abs) of samples containing bacterial supernatant, assay substrate solution (p-nitrophenyl-N-acetyl-β-D-glucosaminide), and reaction buffer at 405 nm over time (hours). (SA=Staphylococcus aureus; SE=Staphylococcus epidermidis; SM=Serratia marcescens; SS=Streptococcus salivarius; EC=Escherichia coli; PA=Pseudomonas aeruginosa; EF=Enterococcus faecalis)

FIG. 8 is a graph showing the change in absorbance of samples containing bacteria supernatant (or water), substrate and reaction buffer over time (in hours). Supernatant from *Enterococcus faecalis* (*E. faecalis*) cultures reacted with the substrate, giving rise to a color change over the course of the reaction. None of the other culture supernatants were distinguishable from the water control. Thus, this assay can be used as a specific detection system for *Enterococcus faecalis*. Modification of PNP-AGA by a bacterial sample indicates that the bacteria can be *Enterococcus*. In addition, the absence of modification of PNP-AGA by a bacterial sample can indicate that the bacteria is not *Enterococcus*.

Example 11

Detection of the Presence of *Streptococcus salivarius* Using a Beta-Galactosidase Assay Most bacterial species express beta-galactosidase as a cytoplasmic enzyme for the metabolism of lactose as an energy source. Certain species of *Streptococcus*, however, display the enzyme on the surface of the cell. A labeled synthetic molecule that acts as a substrate for beta-galactosidase, (for example, ortho nitrophenyl b-D-galactopyranoside (ONP-GP)) could thus be used as a means of detecting streptococci in the environment.

To determine the presence or absence of bacteria in a sample, mid-log phase bacterial supernatants were obtained as described in Example 2. A substrate solution containing the labeled synthetic substrate ortho-nitrophenyl-b-D-galactopyranoside (ONPG) dissolved in 50% DMSO to a concentration of 20 mM was prepared. In addition, a reaction solution containing 20 mM $NaPO_4$ (pH 7) with 200 mM NaCl. The beta-galactosidase assay was carried out as follows. Five hundred µL of reaction buffer, 450 µL of bacterial supernatant, and 50 µL of substrate solution were combined in a reaction tube to give 1 mL total volume. A control contained 450 µL of water in place of the supernatant. The samples were incubated at 37° C. and absorbance at 420 nm was measured hourly.

Figure 9:
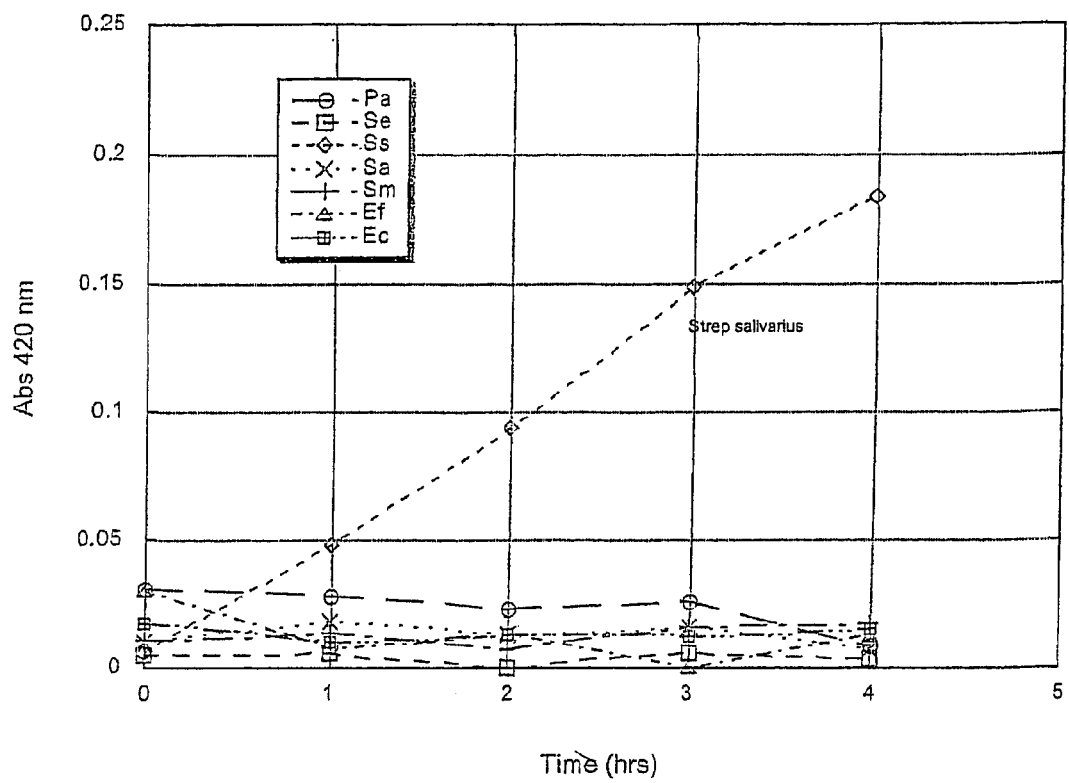
FIG. 9 is a graph of the absorbance (Abs 420 nm) of samples containing bacterial supernatant, assay substrate solution (ortho-nitrophenyl-N-acetyl-β-D-galactopyranoside), and reaction buffer at 420 nm over time (hours). (SA=Staphylococcus aureus; SE=Staphylococcus epidermidis; SM=Serratia marcescens; SS=Streptococcus salivarius; EC=Escherichia coli; PA=Pseudomonas aeruginosa; EF=Enterococcus faecalis)

FIG. 9 is a graph of the absorbance of the samples at 420 nm over time (in hours). As shown in FIG. 9, most culture supernatants did not show signs of beta-galactosidase activity. *Streptococcus salivarius* (*S. salivarius*) supernatant however, did react with the substrate, most likely because of surface expressed beta-galactosidase. Since most of the enzyme remains attached to the cell surface, the reactivity may be due to enzyme that has cleaved from the surface, or from cells that carried over into the supernatant. Accordingly, alternatively, the assay can be performed on a cell suspension, rather than on the cell supernatant.

In this assay, *Streptococcus salivarius* reacted with the substrate, while other species did not. This assay forms the basis of a specific test for *Streptococcus salivarius*. Modification of ONPG by a bacterial sample indicates that the bacteria can be *Streptococcus*. In addition, the absence of modification of ONP-GP by a bacterial sample can indicate that the bacteria is not *Streptococcus*.

Example 12

A Biosensor for Detection of *Staphylococcus epidermidis*

Figure 10:
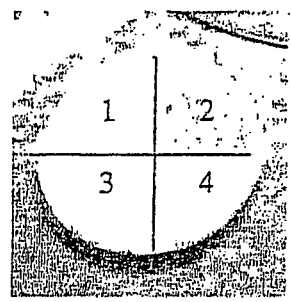
FIG. 10 is a scanned image of a 2.5 cm glass microfiber filter (Whatman GF/A), soaked with p-nitrophenyl caprate (in ispropanol) to which 4 different samples have been applied. In Quadrant #1, Staphylococcus aureus was applied; in Quadrant #2, Staphylococcus epidermidis was applied; in Quadrant #3 Streptococcus salivarius was applied, and in Quadrant #4, media was applied as a control. The presence of a yellow dye (gray shading), indicating modification of the substrate by an enzyme in the bacteria is shown in Quadrant #2.

An example of a biosensor for the detection of an enzyme secreted by *Staphylococcus epidermidis* (*S. epidermidis*), and therefore, for the detection of *Staphylococcus epidermidis* now follows. A 100 mM solution of 20 mM p-nitrophenyl Caprate (in ispropanol) was applied to a 2.5 cm glass microfiber filter (Whatman GF/A). The isopropanol was allowed to evaporate at room temperature for 30 minutes, leaving the substrate bound to the filter. After the filter was completely dry, a single drop of bacterial culture was applied to each quadrant of the filter. In Quadrant #1, *Staphylococcus aureus* was applied; in Quadrant #2, *Staphylococcus epidermidis* was applied; in Quadrant #3 *Streptococcus salivarius* was applied, and in Quadrant #4, media was applied as a control. The filter was incubated at 37° C. for 30 minutes, and detection of a yellow dye, indicating modification of the substrate by an enzyme in the bacteria was detected. As shown in FIG. 10, no modification of the labeled substrate was detected in Quadrants # 1, #, 3, or #4. Modification of the labeled substrate was detected in Quadrant # 2. These results demonstrate how a biosensor can be used to detect the presence or absence of a microorganism in a sample.

Example 13

Detection of the Presence of *Pseudomonas aeruginosa* Using a Protease Assay or a Lipase Assay Three peptide substrates of *Pseudomonas aeruginosa* (*P. aeruginosa*) were identified and synthesized. The three peptides are shown in Table 1.

TABLE 1

| Peptide | Origin | Function |
|---------|--------|----------|
| papa1 | PepA | Exoprotein |
| pala1 | LasA | Elastase Gene Cluster |
| paga1 | Poly-gly from *Staphylococcus* | Pathogen:Pathogen Interactions |

The peptide substrates used here were labeled with the fluorescent probe edans (5-((2-aminoethyl)amino)naphthalene-1-sulfonic acid) and the quencher dye molecule dabcyl ((4-(4-(dimethylamino)phenyl)azo)benzoic acid). The labeled peptide sequences used were as follows:

```
PAPA1  Edans - KAAHKSALKSAE - Dabcyl  (SEQ ID NO: 3)

PALA1  Edans - KHLGGGALGGGAKE -        (SEQ ID NO: 4)
       Dabcyl

PAGA1  Edans - KHLGGGGGAKE - Dabcyl.  (SEQ ID NO: 5)
```

Additional substrates tested for their suitability in detecting *P. aeruginosa* were the para-nitrophenyl lipid ester substrates shown in Table 2.

TABLE 2

| Lipid Ester | Origin | Length |
|-------------|--------|--------|
| propionate | synthetic | C3 |
| butyrate | synthetic | C4 |
| caproate | synthetic | C6 |
| and others | synthetic | up to C18 |

The para-nitrophenyl lipid ester substrates were used at a concentration of 10 mM dissolved in isopropanol.

Protease Assay

Figure 11:
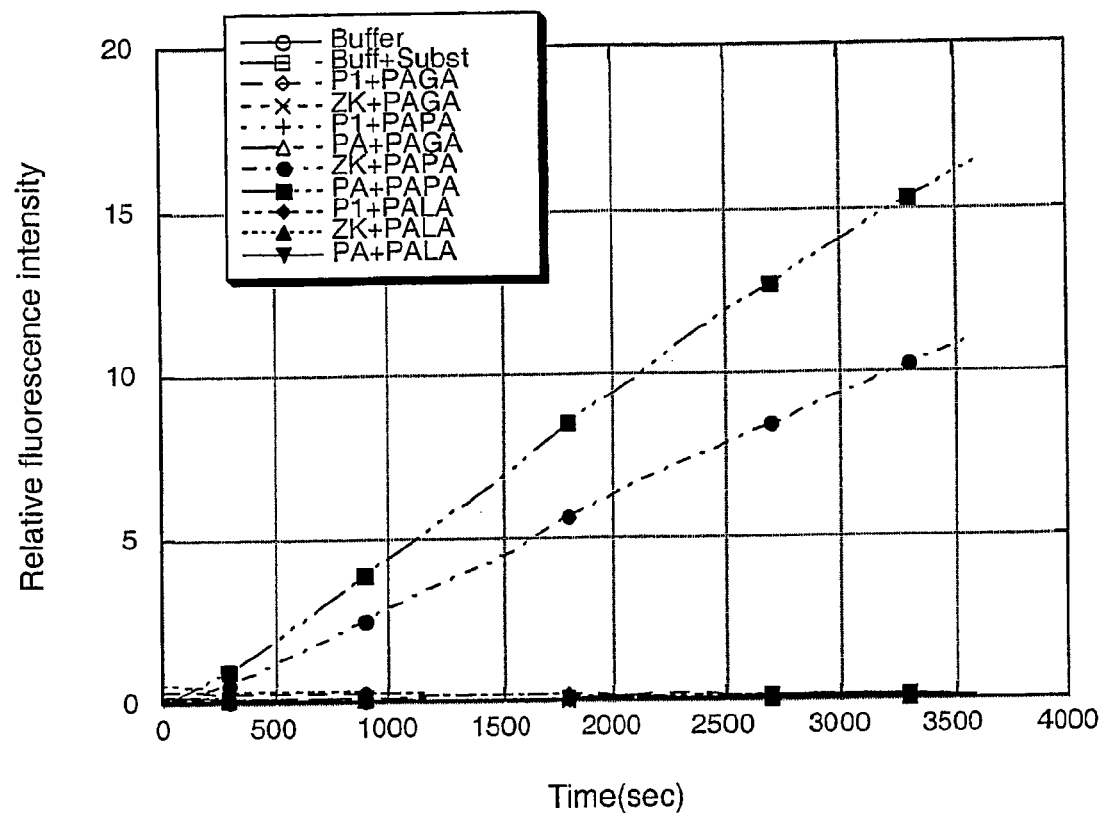
FIG. 11 is a graph of detection of enzymatic cleavage (relative fluorescent intensity) of papa1 (papa), pala1 (pala), and paga1 (paga) over time (seconds) in samples containing Pseudomonas strains P1, PA14 (PA), and ZK45 (ZK), or buffer alone, or buffer plus substrate.

A protease assay for detecting the presence of *P. aeruginosa* was carried out as follows. Three strains of *P. aeruginosa* bacteria (P1, a "student friendly" strain, PA14, the accepted standard strain for virulence models, and ZK45, a clinical isolate for Children's Hospital in Boston, Mass.) were grown in an incubator overnight at 37° C. in 5 mL of BHI (Brain Heart Infusion) media. The resulting cultures were spun down by centrifugation and the supernatants were collected. The assays were performed in 20 mM tris buffer (pH 7.5) with 150 mM NaCl added. The reactions were carried out with 3 µL of supernatant and 7 µL of labeled substrate (as indicated in FIG. 11) in 100 µL total volume at 37° C. The reaction was followed by measuring absorbance at 485 nm on a fluorimetric plate reader. The results are shown in FIG. 11. As shown in FIG. 11, the papa1 peptide substrate was cleaved by *Pseudomonas*.

Figure 12:
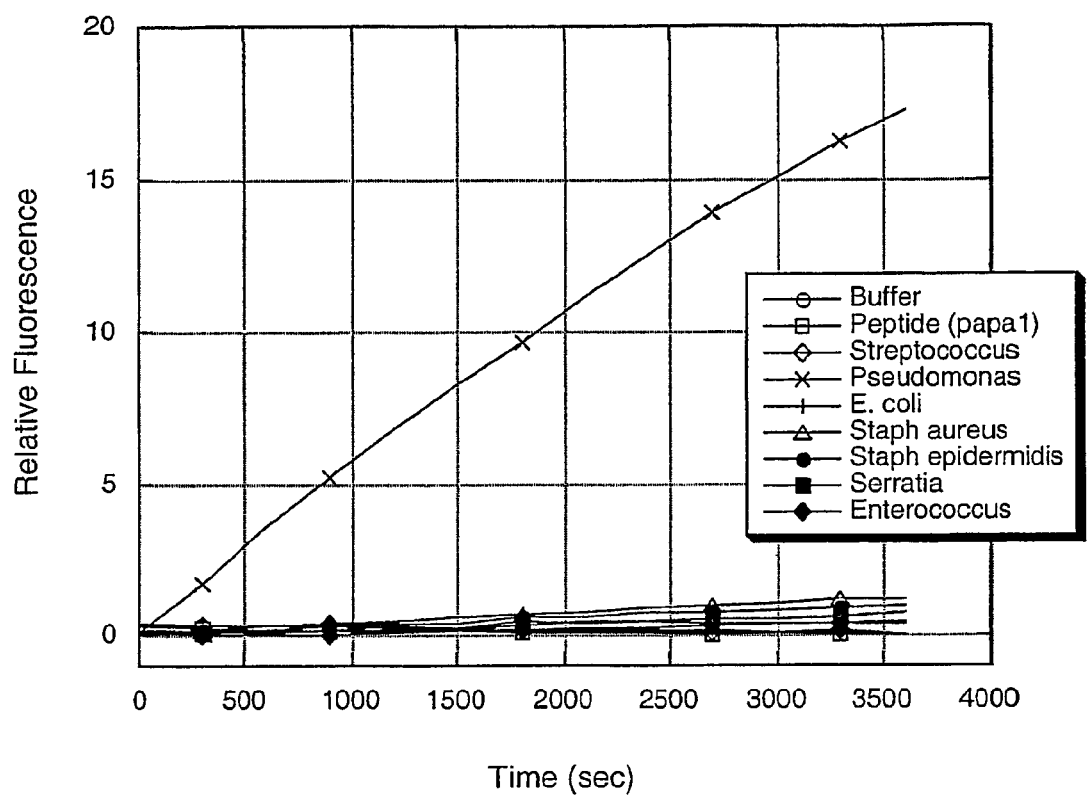
FIG. 12 is a graph of detection of enzymatic cleavage (fluorescence) of papa1 (papa) over time (seconds) in samples containing buffer only, buffer plus papa1, S. pyogenes plus papa1 (Streptococcus), P. aeruginosa strain PA14 plus papa1 (Pseudomonas), E. coli plus papa1 (E. coli), S. aureus plus papa1 (Staph aureus), S. epidermidis plus papa1 (Staph epidermidis), S. marcescens plus papa1 (Serretia), or E. faecalis plus papa1 (Enterococcus).

This protease assay was repeated using various strains of bacteria, including *S. pyogenes*, *P. aeruginosa* strain PA14, *S. epidermidis*, *S. marcescens*, and *E. faecalis* and the peptide substrate papa1. As shown in FIG. 12, the protease assay was specific for detection of *P. aeruginosa*.

Figure 13A:
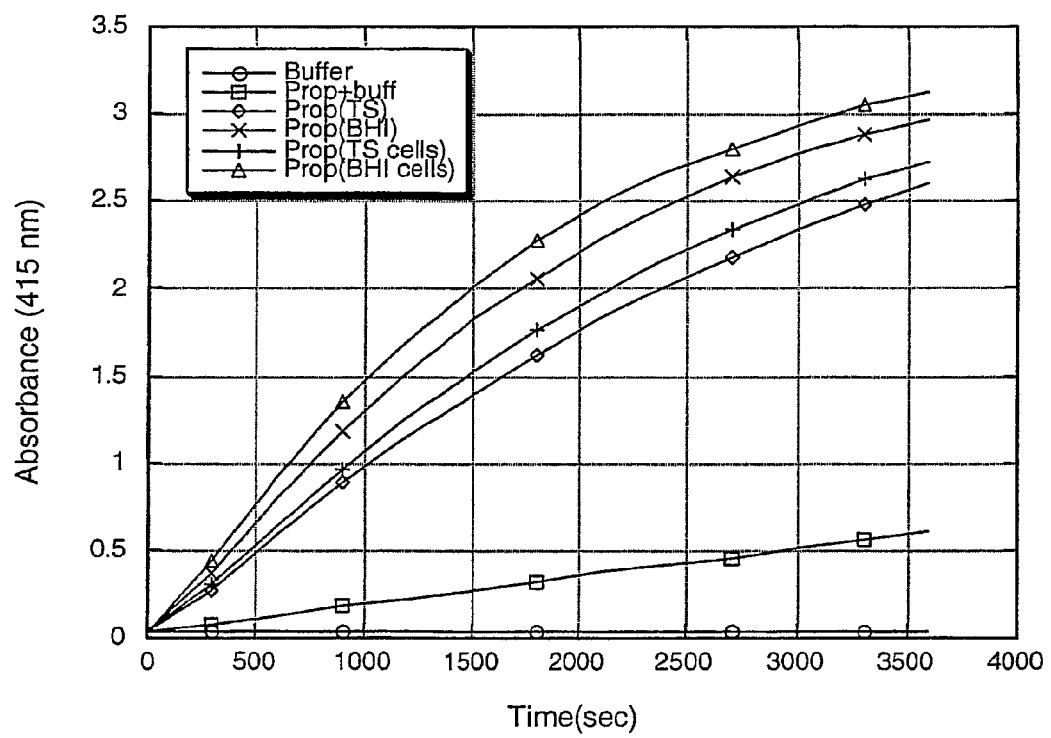
FIG. 13A is a graph of the hydrolysis of labeled propionate substrate (change in absorbance) over time (seconds) for samples containing buffer only, substrate plus buffer, substrate plus supernatant from P. aeruginosa PA14 grown in tryptic soy media (Prop(TS)); substrate plus supernatant from P. aeruginosa PA14 grown in Brain Heart Infusion media (Prop(BHI)); substrate plus P. aeruginosa PA14 grown in tryptic soy media (Prop(TS cells)); or substrate plus P. aeruginosa PA14 grown in Brain Heart Infusion media (Prop(BHI cells)).
Figure 13B:
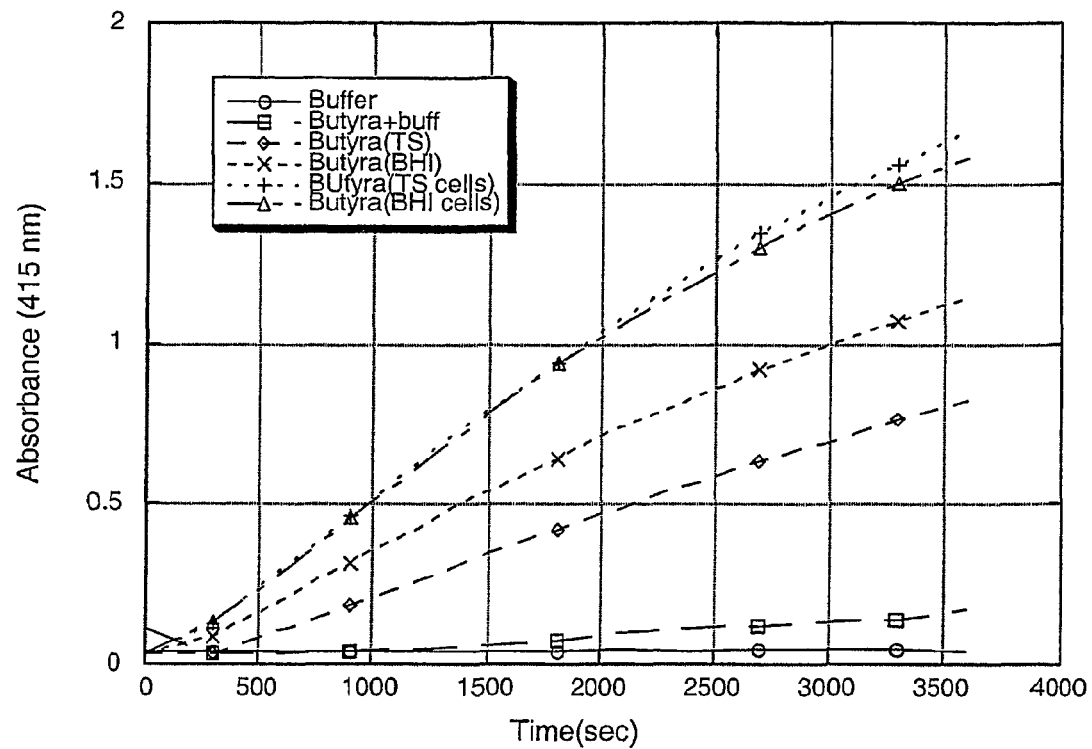
FIG. 13B is a graph of the hydrolysis of labeled butyrate substrate (change in absorbance) over time (seconds) for samples containing buffer only, substrate plus buffer, substrate plus supernatant from P. aeruginosa PA14 grown in tryptic soy media (Butyra(TS)); substrate plus supernatant from P. aeruginosa PA14 grown in Brain Heart Infusion media (Butyra(BHI)); substrate plus P. aeruginosa PA14 grown in tryptic soy media (Butyra(TS cells)); or substrate plus P. aeruginosa PA14 grown in Brain Heart Infusion media (Butyra(BHI cells)).
Figure 13C:
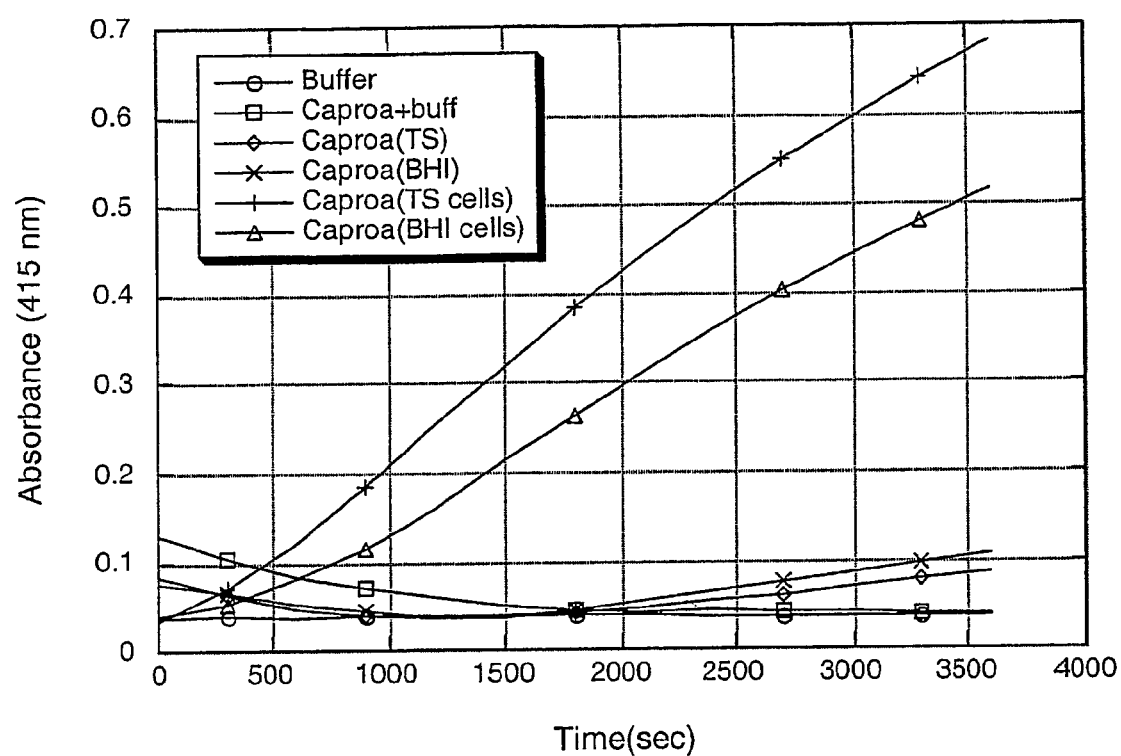
FIG. 13C is a graph of the hydrolysis of labeled caproate substrate (change in absorbance) over time (seconds) for samples containing buffer only, substrate plus buffer, substrate plus supernatant from *P. aeruginosa* PA14 grown in tryptic soy media (Caproa(TS)); substrate plus supernatant from *P. aeruginosa* PA14 grown in Brain Heart Infusion media (Caproa(BHI)); substrate plus *P. aeruginosa* PA14 grown in tryptic soy media (Caproa(TS cells)); or substrate plus *P. aeruginosa* PA14 grown in Brain Heart Infusion media (Caproa(BHI cells)).

A lipase assay for detecting the presence of *P. aeruginosa* in a sample was carried out as follows. Bacteria from the *P. aeruginosa* strain PA14 were grown in an incubator overnight at 37° C. in 5 mL of TS (Tryptic Soy Broth with dextrose) or BHI (Brain Heart Infusion) media. The resulting cultures were separated into two samples: one sample was used as a culture of cells and media, and the other sample was spun down by centrifugation and the supernatant was collected. The lipase assays were run in 20 mM tris buffer (pH 7.5) with 150 mM NaCl added. The reaction was carried out with 10 µL of labeled substrate (propionate (FIG. 13A), butyrate (FIG. 13B), or caproate (FIG. 13C)) in 100 µL total volume at 37° C. In the indicated samples, the reaction included 10 µL of bacterial supernatant or 10 µL of bacterial cell culture. The reaction was followed by measuring absorbance at 415 nm on a calorimetric plate reader. The results are shown in FIGS. 13A-13C). As shown in FIGS. 13A-13C, nitrophenyl substrates (C3-C6) are suitable for detecting *P. aeruginosa*.

Additional studies involving detection of *P. aeruginosa* using the above-described lipase assay were carried out as follows. The PA14 *P. aeruginosa* strain, *Serratia*, *S. aureus*, *S. epidermidis*, *Streptococcus*, *Enterococcus*, *E. coli*, and *S. Pyogenes* were each grown in an incubator overnight at 37° C. in 5 mL of BHI (Brain Heart Infusion) media. The resulting cultures were spun down by centrifugation and the supernatant was collected. This set of assays was run in 20 mM tris buffer (pH 7.5) with 150 mM NaCl added. The reaction was carried out with 10 µL of substrate in 100 µL total volume at 37° C. In the indicated samples (FIG. 14) the reaction included 10 µL of bacterial supernatant. The reaction was followed by measuring the absorbance at 415 nm on a calorimetric plate reader. The results are shown in FIG. 14.

Figure 14:
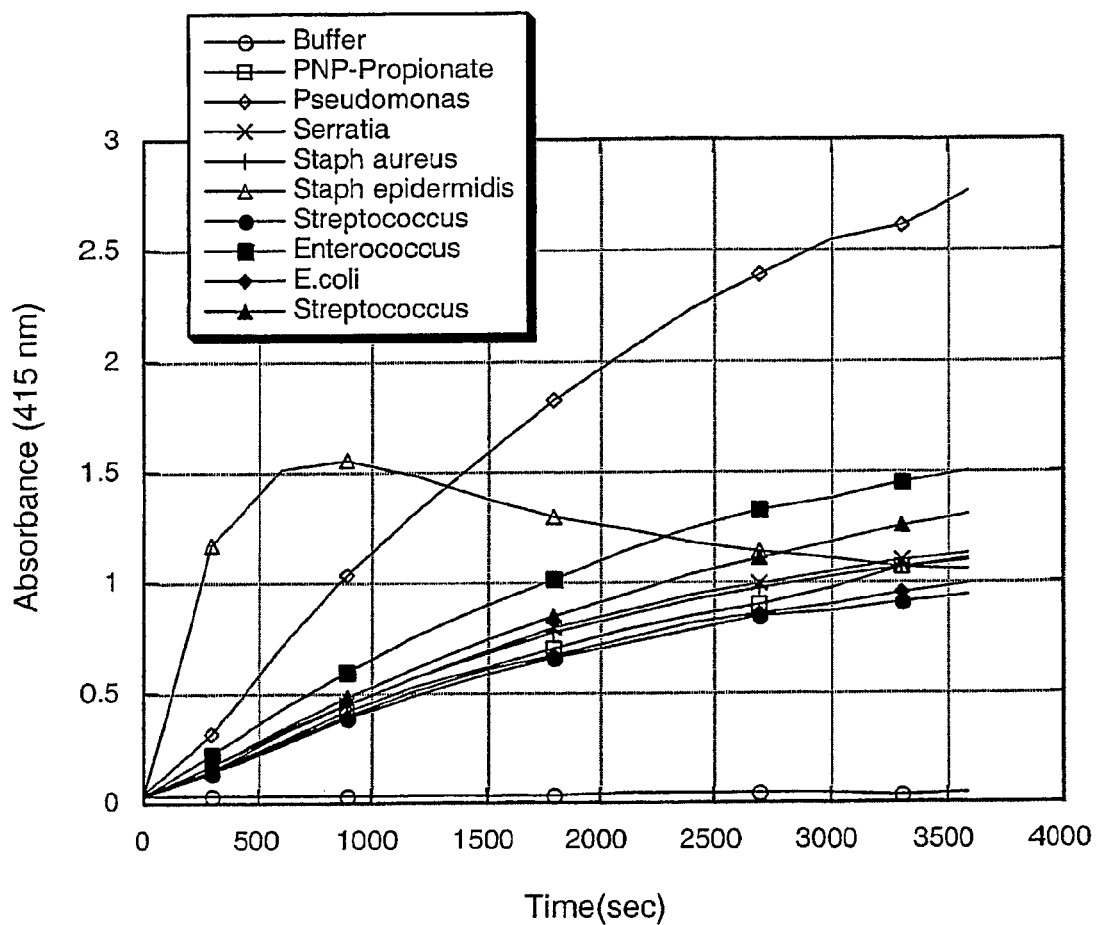
FIG. 14 is a graph of the hydrolysis of labeled propionate ester substrate (absorbance) over time (seconds) in samples containing buffer, buffer plus substrate (PNP-Propionate) or substrate plus the following bacteria: PA14 *P. aeruginosa* strain (*Pseudomonas*), *Serratia*, *S. aureus* (*Staph aureus*), *S. epidermidis* (*Staph epidermidis*), *Streptococcus* (*Streptococcus* ●), *Enterococcus* (*Enterococcus*), *E. coli*, and *S. Pyogenes* (*Strep P* ▲).

As shown in FIG. 14, over time, *P. aeruginosa* demonstrated the greatest activity on the substrate. The reaction conditions can varied to further separate the reactivity of *Pseudomonas* in comparison to other species, if a faster reaction time is desired. A large change in the reactivity of a lipase enzyme can be achieved, for example, by modification of the reaction solution to more closely match the environment of the lipid membrane.

Additional studies can be carried out on the substrates to examine the cross reactivity of the substrate with additional reaction agents or with the types of molecules that could be present in a wound environment, for example, serum during the detection of *P. aeruginosa*. If the substrates cross-react with serum, it may be desirable to modify the substrate or the reaction conditions, using methods known to one of skill in the art, to lower the cross reactivity.

Example 14

Detection of the Presence of Microorganisms by Detecting DNA Metabolism Enzymes As described herein, DNA metabolism enzymes is a class of enzymes identified in the bioinformatics search of genes that are in common among wound pathogens Based on this knowledge, the types of DNA metabolism activities (exonuclease and endonuclease) that can be detected with wound pathogens grown in culture were determined as follows. Ten μg of pUC19 DNA was linearized by digestion with EcoRI enzyme. Ten mL overnight cultures of *S. aureus, E. faecalis, E. coli, P. aeruginosa, S. salivarius, S. marcescens*, and *S. epidermidis* were then grown. Five μL of DNA was added to 70 μL of bacterial cells. The samples were then incubated for the time periods of 1 hr, 3 hr, and overnight. At the indicated time intervals an aliquot of the sample was removed and placed in a new tube. The reaction was stopped with 10× DNA sample buffer and the samples were stored at −20° C. before running on a 1.2% TBE agarose gel (80V, constant power). The DNA metabolism activities by the various bacterial cultures are shown in FIG. 15.

Figure 15:
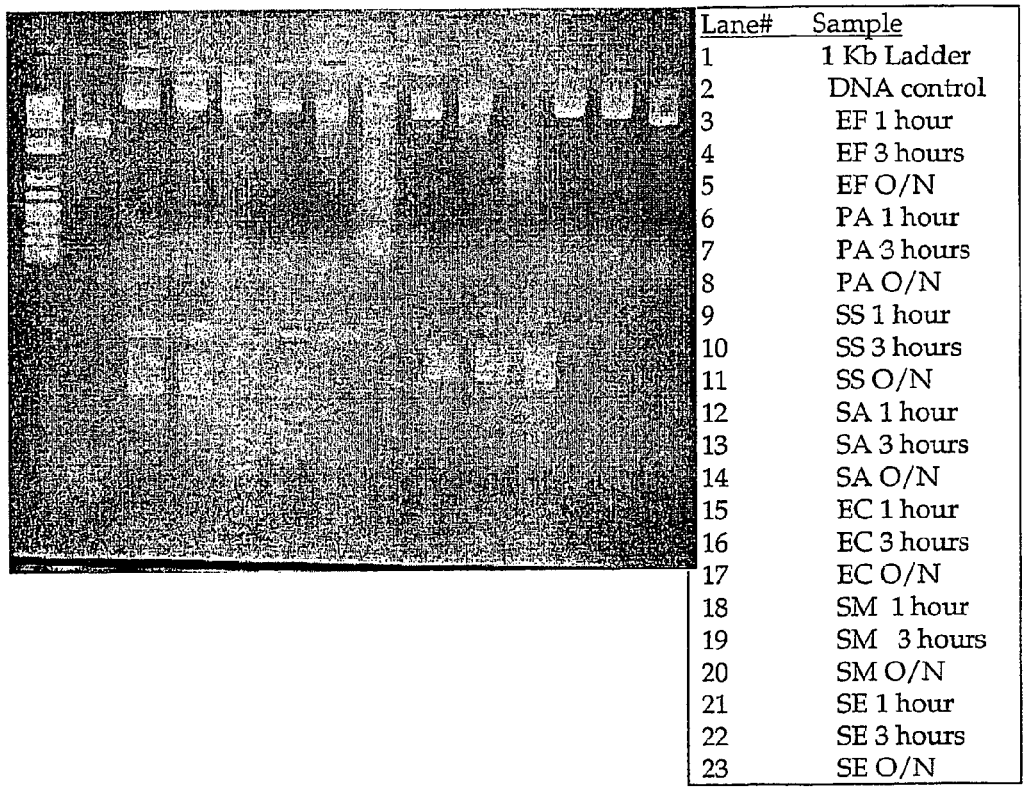
FIG. 15 is a scanned image of an agarose gel electrophoresed with 1 Kb ladder, DNA control (circular pUC19 plasmid), or linearized pUC19 DNA further cleaved by DNA metabolism enzymes in *Staphylococcus aureus* (SA), *Enterococcus faecalis* (EF), *E. coli* (EC), *Pseudomonas aeruginosa* (PA), *Streptococcus salivarius* (SS), *Serratia marcescens* (SM), or *Staphylococcus epidermidis* (SE) for 1 hour, 3 hours, or overnight (O/N). Lane numbers and corresponding samples are indicated.

As shown in FIG. 15, all bacteria tested had some DNA metabolism activity. Bacteria with pronounced endonuclease activity included *S. aureus, S. epidermidis, E. faecalis*, and *P. aeruginosa*. Bacteria with strong exonuclease activity includef *S. marcescens, P. aeruginosa, E. coli*, and *Streptococcus*. In addition, *Staphylococcus* (*aureus* or *epidermidis*) had little exonuclease activity.

Figure 16:
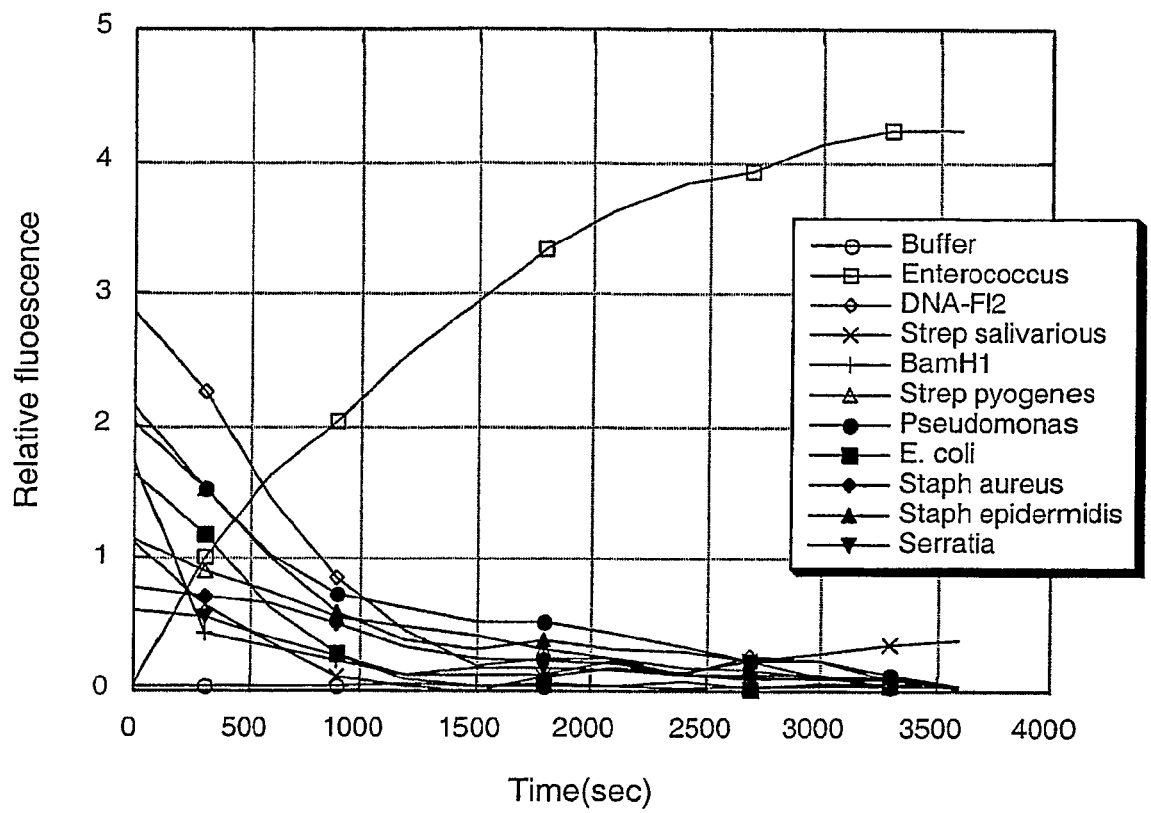
FIG. 16 is a graph of the DNA metabolic activity (relative fluorescence) of labeled probe over time (seconds) in samples containing buffer, probe only (DBAF12), or probe plus *Enterococcus*, *S. Salivarius* (*Strep salivarius*), probe administered BamHI enzyme (BamHI), *S. pyogenes* (*Strep pyogenes*), *Pseudomonas*, *E. coli*, *S. aureus* (*Staph aureus*), *S. epidermidis* (*Staph epidermidis*) or *Serratia*.

Another method for detecting DNA metabolism activity is to generate synthetic colorimetric and fluorescent DNA probes that can indicate DNA hydrolysis (exonuclease and endonuclease activity). The method was carried out as follows. Two complementary oligonucleotides were generated. One oligonucleotide was labeled with self-quenching fluorescent labels, while the other primer remained unlabeled. The sequences of the oligonucleotides were as follows: Unlabeled Sequence 5'-CCTCTCGAGGATCCACTGAAT-TCCT-3 (SEQ ID NO: 6); and Labeled Sequence FL-5'-AGGAATTCAGTGGATCCTCGAGAGG-3'-FL (SEQ ID NO: 7). Bacteria (*E. faecalis, S. Salivarius, S. pyogenes, P. aeruginosa, E. coli, S. aureus, S. epidermidis*, and *S. marcescens*) were grown in an incubator overnight at 37° C. in 5 mL of BHI (Brain Heart Infusion) media. The culture was spun down by centrifugation and the supernatant was collected. The fluorescent labeled primer and its unlabeled complement were dissolved in water at a concentration of approximately 1 mg/mL. The primers were heated to melting temperature for 2 minutes at 92° C., then allowed to anneal for 5 minutes at 43° C. After annealing, the DNA substrate was added to the reaction buffer (20 mM tris (pH 7.4) with 150 mM NaCl) and incubated at 37° C. for 10 minutes. The reaction was carried out with 7 μL of culture supernatant and 3 μL of DNA substrate in 100 μL total volume at 37° C. The reaction was followed using a fluorimetric plate reader using an excitation wavelength of 485 nm and an emission wavelength of 538 nm. The results of this assay are shown in FIG. 16. The labeled DNA probe detected specific DNA metabolic activity associated with *Enterococcus*. Another probe that can be used to detect the presence of bacteria with DNA metabolism activity is: Rh-5'-AGGAATTCAGTGGATCCTCGAGAGG-3'-FL (SEQ ID NO: 8) and its complement, which, when annealed, is designed to give both colorimetric and fluorimetric signals upon cleavage of the DNA sequence.

Example 15

Development of Biosensor Surfaces

The attachment of molecules to surfaces can be performed by the use of several different types of interactions. Typically, proteins can be attached to surfaces using hydrophobic, electrostatic, or covalent interactions. There are many commercially available membranes and resins with a variety of surface properties. Surfaces can also be chemically modified to provide the required surface properties.

Commercially available transfer membranes exist for protein and peptide binding. They consist of positively and negatively charged polymers such as ion exchange membrane disc filters and resins. Nitrocellulose membranes offer hydrophobic and electrostatic interactions. Glass fiber membranes offer a hydrophobic surface that can easily be chemically modified to add functional groups. There are also modified polymer membranes that offer reactive functional groups that covalently bind proteins and peptides.

It is also possible to utilize various functional groups on membranes or resins and a crosslinking agent to covalently link to proteins. Crosslinking reagents contain two reactive groups, thereby providing a means of covalently linking two target functional groups. Common functional groups to target on proteins are amine, thiol, carboxylic acid, and alcohol groups that are used to form intramolecular crosslinks. Crosslinking agents can be homobifunctional or heterobifunctional and a selection of crosslinking agents of various lengths are commercially available.

Initially the peptides studied were designed as substrates for bacterial assay development using fluorescence energy transfer (Edans and Dabcyl) for detection. papa1, which is selective for *Pseudomonas*, is an example of such a substrate, and is described herein.

In order to develop substrates specifically for surface immobilization, several versions of the papa1 peptide substrate were made. The peptides were designed to include lysine groups (amine functional group) at one end of the peptide in the case of papa2. The addition of two lysine groups (KK) at one end of the peptide serve as a "tag" and provide suitable groups for attachment to surfaces through techniques such as electrostatic interactions or through covalent attachment. The peptide papa3 was designed to include a cysteine group (C) and three histidine groups (HHH) at one end. The addition of a cysteine provides another suitable group or tag to perform covalent attachments through the thiol group. The inclusion of three histidine groups also provides the potential for attachment to nickel resins.

The peptide sequences for papa1 was modified as shown:

```
                                         (SEQ ID NO: 3)
papa1    (dabcyl-K)AAHKSALKSA(E-edans)

(SEQ ID NO: 9)
papa2    KKAS(E-edans)AAHKSALKSAE(K-dabcyl)

(SEQ ID NO: 10)
papa3    CHHHAS(E-edans)AAHKSALKSAE(K-dabcyl)
```

The pre-peptide tags were added to the original papa1 sequence, as shown above, to allow for attachment to a surface.

Figure 17A:
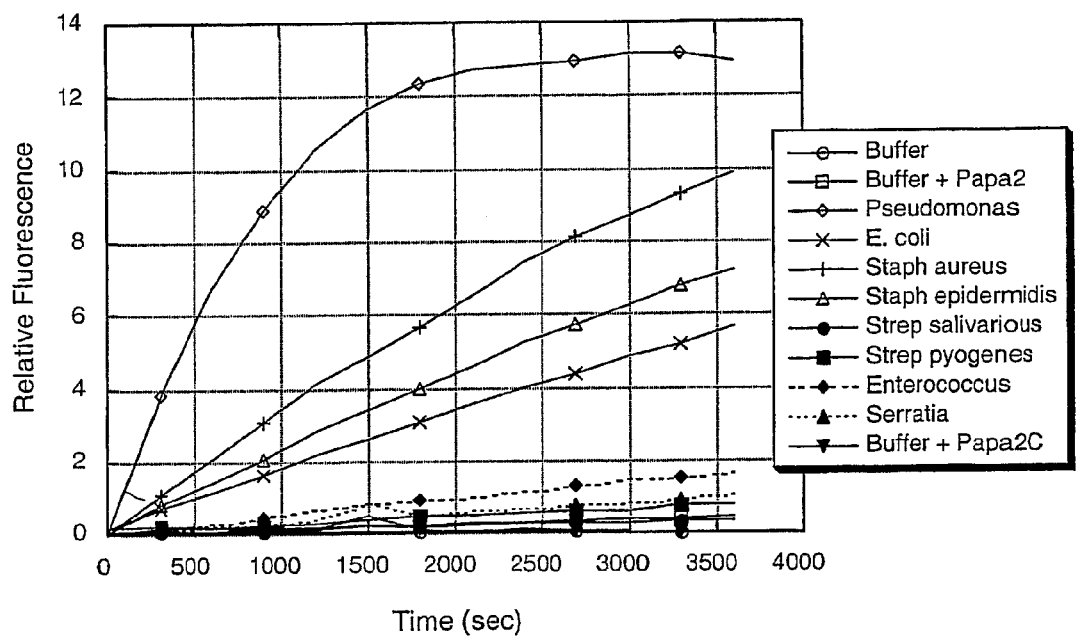
FIG. 17A is a graph of cleavage of protease substrate papa2 or papa2C (relative fluorescence) over time (seconds) in samples containing buffer, buffer plus papa2, buffer plus papa2C, or supernatants from *Pseudomonas*, *E. coli*, *S. aureus* (*Staph aureus*), *S. epidermidis* (*Staph epidermidis*), *S. Salivarius* (*Strep salivarius*), *S. pyogenes* (*Strep pyogenes*), *Enterococcus*, or *Serratia* plus papa2.

The protease assay described herein for detection of *P. aeruginosa* was run with the modified version of papa1. Bacteria (*Pseudomonas, E. coli, S. aureus, S. epidermidis, S. salivarius, S. pyogenes, Enterococcus*, and *Serratia*) were grown in an incubator overnight at 37° C. in 5 mL of BHI (Brain Heart Infusion) media. Each of the resulting cultures was spun down by centrifugation and the supernatant was collected. The assays were run in 20 mM tris buffer (pH 7.4) with 150 mM NaCl added. The reaction was carried out with 7 μL of supernatant and 3 μL of peptide substrate (5 mg/mL in water) in 100 μL total volume at 37° C. The reaction was followed on a fluorimetric plate reader using an excitation wavelength of 355 nm and an emission wavelength of 485 nm. The results are shown in FIG. 17A. As shown in FIG. 17A, this protease assay showed the greatest fluorescence in the sample containing *Pseudomonas*.

Figure 17B:
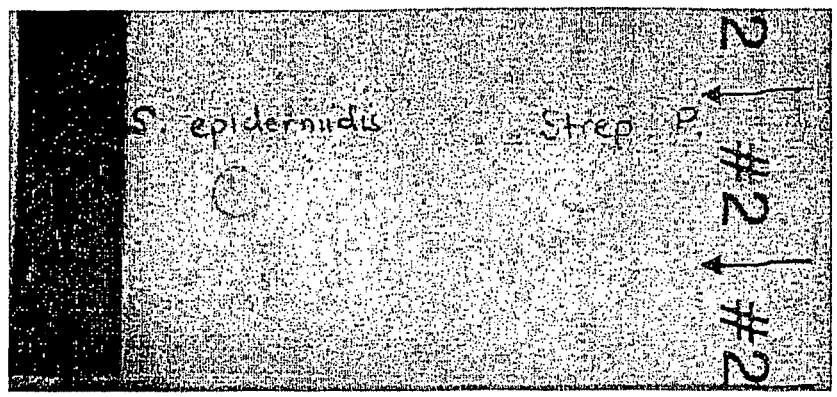
FIG. 17B is a scanned image of the detection of *S. epidermidis* and lack of detection of *S. pyogenes* on a biosensor in which the peptide substrates 5-bromo-4-chloro-3indolyl butyrate and 5-bromo-4-chloro-3indolyl caprylate were bound to a solid substrate (glass microfiber filter) through hydrophobic interactions.

Hydrophobic interactions make use of the non-ionic packing that occurs in a polar solvent such as water and such interactions can be used in the production of biosensors for detection of pathogens. The substrates 5-bromo-4-chloro-3indolyl butyrate and 5-bromo-4-chloro-3indolyl caprylate can be spotted onto a glass microfiber filter to make a sensor. Upon spotting the filter with a small amount of *Staphylococcus* (*aureus* or *epidermidis*) culture medium the color of the filter will turn blue in approximately 15 minutes. An example of this assay is shown in FIG. 17B, where the dark spot corresponding to *S. epidermidis* indicates detection of that pathogen in this assay. The assay did not detect *S. pyogenes*.

Figure 17C:
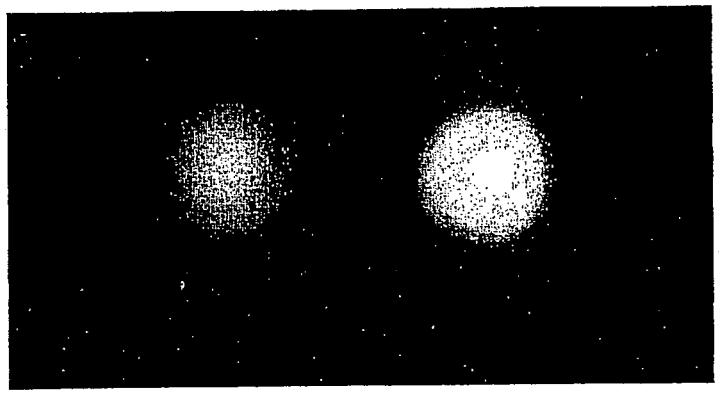
FIG. 17C is a scanned image of the detection of *Pseudomonas* (right) on a biosensor in which the peptide substrate papa2 is bound to a solid substrate (positively charged membrane) through electrostatic interactions and exposed to *Pseudomonas* (right) or BHI media containing no bacteria (left).

Electrostatic interactions make use of the charges on the peptide or chromophore to bind it to a surface to make a biosensor. For example, ion exchange membranes with a strong negative (ICE450) or positive (SB-6407) charge are available from Pall Gelman Laboratory, Ann Arbor, Mich. It is possible to bind the peptide substrates through interactions with their charged groups. The peptide substrate papa2, as described herein, was spotted onto a positively charged membrane and exposed to *Pseudomonas* culture medium. As shown in FIG. 17C, upon cleavage of the peptide yellow fluorescence (indicated by a bright spot, right side of FIG. 17C) was observed.

Metal chelate (affinity binding) interactions can provide a stronger bond to biological molecules. A his-tag built into the peptide substrate can be used to allow linkage to a nickel binding resin. The resin is incubated with a suitable culture for 30 minutes at 37° C. After centrifugation the buffer is removed and the pelleted resin is imaged. The fluorescence produced by the peptide is then detected.

Lysine peptide tags, for example, papa2 can be used to link to a surface such as UltraBind™ (Pall Gelman Laboratory, Ann Arbor, Mich.). UltraBind is a polyethersulfone membrane that is modified with aldehyde groups for covalent binding of proteins. Proteins are directly reacted with the UltraBind surface. It is also possible to link proteins or peptides to the surface using cross linker chains. For example, the carbodiimide, EDC (1-ethyl-3-(3-dimethylaminopropyl)carbodiimide, hydrochloride) is commonly used to link carboxylic acid groups to amines. The linking of the peptide with a cross linking agent allows the choice of a linker chain to extend the peptide off the surface of the membrane while still covalently binding it. The linking of the peptide through a cross linker can be optimized to make the peptide available to the bacterial enzymes. This allows for optimization of the reaction time of the biosensor since peptide availability is directly related to this parameter.

Example 16

Detection of *Pseudomonas* in Porcine Wound Fluid

In order to test for the presence of enzymatic activity in a wound bacterial protease assay for detection of *P. aeruginosa* was performed on samples obtained from wound infections made in pigs. The bacteria were grown in an incubator overnight at 37° C. in 5 mL of Brain Heart Infusion (BHI) media. Each of the resulting cultures was diluted into sodium phosphate buffer at pH 7.2 with 150 mM NaCl (PBS buffer) to give samples containing $10^5$, $10^4$, and $10^3$ bacteria total in 100 μL. Immediately after surgery to create a series of partial thickness wounds was performed on the pigs, the wound surfaces were treated with calcium chloride solution for a short period and then patted dry. A buffer solution containing diluted bacterial cultures was placed on the surface of the wounds. The wounds were then covered and the infections were allowed to grow for a period of 3 days. After the dressing was removed from the pigs and the wounds were scored for degree of inflammation, 100 μL of PBS buffer was added to the wound surface and the extracted wound fluid was recovered by pipet. Each of the samples was split in half and 50 μL were used to inoculate BHI plates and the other 50 μL were placed in plastic tubes and immediately frozen at –80° C.

The buffer used to dilute the wound fluid in the protease assays was PBS. The reaction was performed in a 96-well microtiter plate. The fluorimetric assays for *P. aeruginosa* was carried out with 20 μL of freshly thawed bacterial culture and 5 μL of papa1 peptide substrate (5 mg/mL in water) diluted into buffer to give 100 μL total volume at 37° C. The reaction was followed on a fluorimetric plate reader using an excitation wavelength of 355 nm and an emission wavelength of 528 nm. The reaction was followed for 1 hour and the results are shown in FIG. 18.

Figure 18:
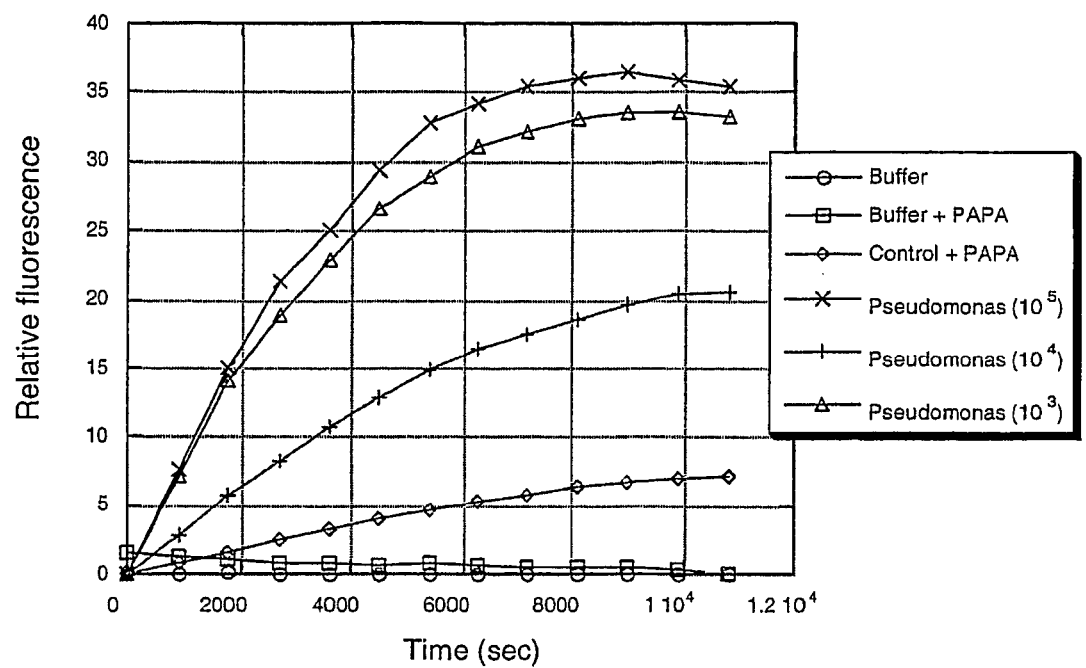
FIG. 18 is a graph of the cleavage of peptide substrate papa1 (relative fluorescence) over time in samples containing buffer, buffer plus papa1, control (no bacteria) plus papa1, or porcine wound extracts from pigs infected with $10^3$, $10^4$ or $10^5$ *P. aeruginosa* (*Pseudomonas*) bacteria plus papa1.

As shown in FIG. 18, the reactivity of the *P. aeruginosa* protease was retained in the wound fluid under these reaction conditions. The samples containing *P. aeruginosa* were detectable using this assay.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for detecting the presence or absence of a wound pathogenic bacterium in a sample of wound fluid obtained from a subject, comprising the steps of:
   (a) contacting the sample with a detectably labeled polypeptide substrate comprising the amino acid sequence of SEQ ID NO: 1, 2, 3, 4, 5, 9 or 10, or an amino acid sequence having at least 99% sequence identity to SEQ ID NO: 1, 2, 3, 4, 5, 9 or 10; and
   (b) detecting the modification or the absence of the modification of said substrate wherein the presence of said modification of said substrate indicates the presence of said wound-pathogenic bacterium in said sample, and the absence of modification of said substrate indicates the absence of said wound-pathogenic bacterium in said sample.

2. The method of claim 1, wherein said substrate is on a solid support.

3. The method of claim 2, wherein said solid support comprises a material required to be free of microbial contaminants.

4. The method of claim 2, wherein said solid support is selected from the group consisting of a wound dressing, a container for holding body fluids, a disk, a scope, a filter, a lens, foam, cloth, paper, a suture, and a swab.

5. The method of claim 4, wherein said container for holding body fluids is selected from the group consisting of a urine collection bag, a blood collection bag, a plasma collection bag, a test tube, a catheter, and a well of a microplate.

6. A method for detecting the presence or absence of *Staphylococcus aureus* in a sample of wound fluid obtained from a subject, comprising the steps of:
   (a) contacting the sample with a detectably labeled polypeptide substrate comprising the amino acid sequence of SEQ ID NO: 1 or having at least 95% sequence identity to SEQ ID NO: 1, the substrate being for a protease produced and/or secreted by said *Staphylococcus aureus* but not produced and/or secreted by a non-wound-pathogenic bacterium or the subject, under conditions that result in modification of said substrate by said protease; and
   (b) detecting the modification or the absence of the modification of said substrate, wherein modification of said substrate indicates the presence of *Staphylococcus aureus* in said sample, and wherein the absence of modification of said substrate indicates the absence of *Staphylococcus aureus* in said sample.

7. The method of claim 6, wherein said substrate is on a solid support.

8. The method of claim 7, wherein said solid support comprises a material required to be free of microbial contaminants.

9. The method of claim 7, wherein said solid support is selected from the group consisting of a wound dressing, a container for holding body fluids, a disk, a scope, a filter, a lens, foam, cloth, paper, a suture, and a swab.

10. The method of claim 9, wherein said container for holding body fluids is selected from the group consisting of a urine collection bag, a blood collection bag, a plasma collection bag, a test tube, a catheter, and a well of a microplate.

* * * * *

SEQUENCE LISTING

<160> NUMBER OF SEQ ID NOS: 10

<210> SEQ ID NO 1
<211> LENGTH: 10
<212> TYPE: PRT
<213> ORGANISM: Artificial Sequence
<220> FEATURE:
<223> OTHER INFORMATION: Peptide that binds to the surface of
      Staphylococcus

<400> SEQUENCE: 1

```
Pro Gly Thr Lys Leu Tyr Thr Val Pro Trp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Peptide substrate of Serratia marcescens

<400> SEQUENCE: 2

Asn Glu Ala Ile Gln Glu Asp Gln Val Gln Tyr Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Peptide substrate of Pseudomonas aeruginosa

<400> SEQUENCE: 3

Lys Ala Ala His Lys Ser Ala Leu Lys Ser Ala Glu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Peptide substrate of Pseudomonas aeruginosa

<400> SEQUENCE: 4

Lys His Leu Gly Gly Gly Ala Leu Gly Gly Gly Ala Lys Glu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Peptide substrate of Pseudomonas aeruginosa

<400> SEQUENCE: 5

Lys His Leu Gly Gly Gly Gly Gly Ala Lys Glu
1               5                   10

<210> SEQ ID NO 6
<211> LENGTH: 25
<212> TYPE: DNA
<213> ORGANISM: Artificial Sequence
<220> FEATURE:
<223> OTHER INFORMATION: Sequence used as a substrate for detection of
      DNA metabolism

<400> SEQUENCE: 6
cctctcgagg atccactgaa ttcct                                          25

<210> SEQ ID NO 7
<211> LENGTH: 25
<212> TYPE: DNA
<213> ORGANISM: Artificial Sequence
<220> FEATURE:
<223> OTHER INFORMATION: Sequence used as a substrate for detection of
      DNA metabolism

<400> SEQUENCE: 7
```

```
aggaattcag tggatcctcg agagg                                              25

<210> SEQ ID NO 8
<211> LENGTH: 25
<212> TYPE: DNA
<213> ORGANISM: Artificial Sequence
<220> FEATURE:
<223> OTHER INFORMATION: Sequence used as a substrate for detection of
      DNA metabolism

<400> SEQUENCE: 8
aggaattcag tggatcctcg agagg                                              25

<210> SEQ ID NO 9
<211> LENGTH: 17
<212> TYPE: PRT
<213> ORGANISM: Artificial Sequence
<220> FEATURE:
<223> OTHER INFORMATION: Peptide substrate of Pseudomonas aeruginosa

<400> SEQUENCE: 9

Lys Lys Ala Ser Glu Ala Ala His Lys Ser Ala Leu Lys Ser Ala Glu
 1               5                  10                  15

Lys

<210> SEQ ID NO 10
<211> LENGTH: 19
<212> TYPE: PRT
<213> ORGANISM: Artificial Sequence
<220> FEATURE:
<223> OTHER INFORMATION: Peptide substrate of Pseudomonas aeruginosa

<400> SEQUENCE: 10

Cys His His His Ala Ser Glu Ala Ala His Lys Ser Ala Leu Lys Ser
 1               5                  10                  15

Ala Glu Lys
```